United States Patent
Mabon et al.

(10) Patent No.: US 12,161,990 B2
(45) Date of Patent: Dec. 10, 2024

(54) EMM-41 COMPOSITION, METHODS OF MAKING AND USES THEREOF

(71) Applicant: ExxonMobil Technology and Engineering Company, Annandale, NJ (US)

(72) Inventors: Ross Mabon, Whitehall, PA (US); Michael A. Marella, Easton, PA (US); Allen W. Burton, Stewartville, NJ (US); Hilda B. Vroman, Piscataway, NJ (US); Kirk D. Schmitt, Pennington, NJ (US); Tom Willhammar, Soha (SE); Hongyi Xu, Taby (SE); Xiaodong Zou, Stockholm (SE); Simon C. Weston, Annandale, NJ (US)

(73) Assignee: EXXONMOBIL TECHNOLOGY AND ENGINEERING COMPANY, Spring, TX (US)

( * ) Notice: Subject to any disclaimer, the term of this patent is extended or adjusted under 35 U.S.C. 154(b) by 677 days.

(21) Appl. No.: 17/311,394

(22) PCT Filed: Nov. 12, 2019

(86) PCT No.: PCT/US2019/060849
§ 371 (c)(1),
(2) Date: Jun. 7, 2021

(87) PCT Pub. No.: WO2020/123070
PCT Pub. Date: Jun. 18, 2020

(65) Prior Publication Data
US 2022/0023827 A1    Jan. 27, 2022

Related U.S. Application Data

(60) Provisional application No. 62/777,852, filed on Dec. 11, 2018.

(51) Int. Cl.
*B01J 20/18* (2006.01)
*B01D 53/02* (2006.01)
(Continued)

(52) U.S. Cl.
CPC .............. *B01J 20/18* (2013.01); *B01D 53/02* (2013.01); *B01J 20/28059* (2013.01);
(Continued)

(58) Field of Classification Search
None
See application file for complete search history.

(56) References Cited

FOREIGN PATENT DOCUMENTS

WO   WO2017/095705 A1   6/2017
WO   WO2017/200607 A1   11/2017

OTHER PUBLICATIONS

Raul F. Lobo et al., "SSZ-26 and SSZ-33: Two Molecular Sieves with Intersecting 10- and 12-Ring Pores", Science, (Dec. 3, 1993), pp. 1543-1546, vol. 262.
(Continued)

*Primary Examiner* — Yun Qian
(74) *Attorney, Agent, or Firm* — Shook, Hardy & Bacon L.L.P.

(57) ABSTRACT

This disclosure relates to EMM-41 materials, methods for making it, and processes for its use. This disclosure also relates to the structure directing agents used in the methods for making the EMM-41 material as well as the synthesis method used to prepare such structure directing agents.

9 Claims, 10 Drawing Sheets

(51) Int. Cl.
- *B01J 20/28* (2006.01)
- *B01J 20/30* (2006.01)
- *C01B 39/46* (2006.01)
- *C01B 39/48* (2006.01)
- *C07D 207/06* (2006.01)
- *C10G 25/03* (2006.01)

(52) U.S. Cl.
CPC ... *B01J 20/28061* (2013.01); *B01J 20/28064* (2013.01); *B01J 20/28071* (2013.01); *B01J 20/3078* (2013.01); *C01B 39/46* (2013.01); *C01B 39/48* (2013.01); *C07D 207/06* (2013.01); *C10G 25/03* (2013.01); *B01D 2253/108* (2013.01); *C01P 2002/72* (2013.01)

(56) References Cited

OTHER PUBLICATIONS

Jiyang Li et al., "Synthesis of new zeolite structures", Royal Society of Chemistry, 2015, pp. 7112-7127, vol. 44.

[010]
Polymorph D
P2
a = 12.5, b = 12.4, c = 45.7 Å, β = 84.0°

[100]
Polymorph D
P2
a = 12.5, b = 12.4, c = 45.7 Å, β = 84.0°

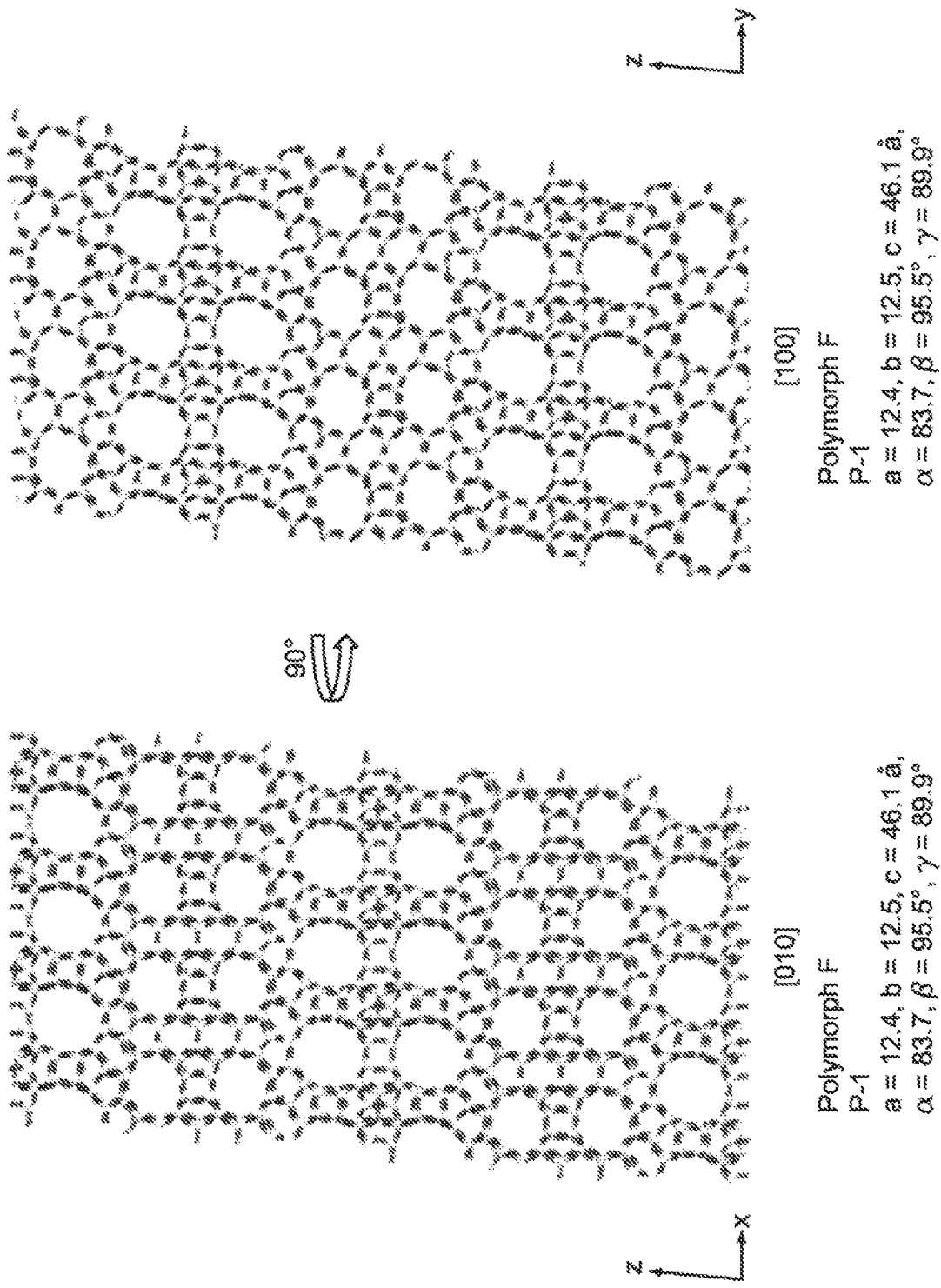

Polymorph G
P4$_2$/mmc
a,b = 12.58, c = 45.58
α = 90.0°, β = 90.0°, γ = 90.0°

Polymorph G
P4$_2$/mmc
a,b = 12.58, c = 45.58
α = 90.0°, β = 90.0°, γ = 90.0°

EMM-41 COMPOSITION, METHODS OF MAKING AND USES THEREOF

CROSS-REFERENCE TO RELATED APPLICATIONS

This application is a national stage application under 35 USC 371 of International Application No. PCT/US2019/060849 filed on Nov. 12, 2019, which claimed the benefit of U.S. Provisional Patent Application No. 62/777,852 filed Dec. 11, 2018.

FIELD

This disclosure relates to a composition of matter, designated as EMM-41, its method of making, and processes for its use. This disclosure also relates to the structure directing agents (SDA) employed in making such EMM-41 composition, as well as the synthesis methods used to prepare this SDA and its precursor compounds.

BACKGROUND

Molecular sieve materials, both natural and synthetic, may be used as adsorbents and have catalytic properties for hydrocarbon conversion reactions. Certain molecular sieves, such as zeolites, are porous crystalline materials which have an ordered structure as determined by X-ray diffraction. Within such materials there are a large number of uniform cavities and pores which may be interconnected by a number of channels. The sizes and dimensions of these cavities and pores are uniform within a specific molecular sieve material and allow for adsorption of molecules of certain sizes while rejecting those of larger dimensions. Due to their ability to adsorb molecules through size selections, molecular sieves and zeolites have many uses including hydrocarbon conversion processes, e.g., cracking, hydrocracking, disproportionation, alkylation, oligomerization, and isomerization.

Molecular sieves are classified by the Structure Commission of the International Zeolite Association according to the rules of the IUPAC Commission on Zeolite Nomenclature. According to this classification, framework type zeolites and other crystalline microporous molecular sieves, for which a structure has been established, are assigned a three letter code and are described in the "Atlas of Zeolite Framework Types", eds. Ch. Baerlocher, L. B. McCusker, and D. H. Olson, Elsevier, Sixth Edition, 2007, which is hereby incorporated by reference.

Molecular sieves may have ordered or disordered structure. Ordered molecular sieves are ordered in three dimensions. When the crystal structure is ordered in all three dimensions, the structure is called an ordered end member structure. Disordered structures, on the other hand, show periodic ordering in less than three dimensions. Representative zeolite families which contain stacking disorders include zeolite beta, SSZ-26/SSZ-33, ITQ-39, ZSM-48, ZSM-5/ZSM-11 and others.

SSZ-26 and SSZ-33 are known large pore zeolites which contain a three-dimensional pore system composed of intersecting 10- and 12-ring pores. (See, Lobo et al., "SSZ-26 and SSZ-33: Two Molecular Sieves with Intersecting 10- and 12-Ring Pores" Science, Vol. 262. no. 5139, pp. 1543-1546, Dec. 3, 1993). These two zeolites can be characterized as members of a family of materials in which the two end members are formed by the stacking of layers in an ABAB sequence or an ABCABC sequence. The framework formed by the ABAB stacking sequence ("polymorph A") is of orthorhombic symmetry and the framework formed by the ABCABC stacking sequence ("polymorph B") is of monoclinic symmetry.

Although many different crystalline molecular sieves have been discovered, there is a continuing need for new molecular sieves with desirable properties for gas separation and drying, organic conversion reactions, and other applications. New molecular sieves can contain novel internal pore architectures, providing enhanced selectivities in these processes.

SUMMARY

Disclosed herein is EMM-41, a crystalline material in calcined form (where at least part of the SDA has been removed) and as-made form (where the SDA has not been removed), as well as methods of their making, and one or more processes for their uses. Also disclosed are the SDAs employed in making such EMM-41 materials, and the synthesis methods use to prepare the SDA and its precursor compounds.

In one aspect, the disclosure provides crystalline materials, wherein part or all of the structure directing agent ("SDA") has been removed (e.g., at least partially calcined EMM-41 material) having at least five (5) of the X-ray diffraction (XRD) peaks in degree 2-theta, shown for example in FIG. 1, and selected from Table 1A, below:

TABLE 1A

| degrees 2-theta (±0.2) | d-spacing (Å) | relative integrated intensity [100 × I/(Io)] |
|---|---|---|
| 7.35* | 12.03 | composite |
| 7.38* | 11.97 | composite (100) |
| 9.04 | 9.78 | 20-40 |
| 10.28 | 8.60 | 9-20 |
| 14.39 | 6.15 | 3-10 |
| 22.77 | 3.90 | 20-40 |

*Peaks form a composite feature.

In another aspect, provided herein is an as-made crystalline material (where the SDA has not been removed) having at least four (4) of the XRD peaks in degree 2-theta, shown for example in FIG. 2 (top), selected from Table 2A:

TABLE 2A

| degrees 2-theta (±0.2) | d-spacing (A) | relative integrated intensity [100 × I/(Io)] |
|---|---|---|
| 7.25* | 12.19 | composite |
| 7.42* | 11.90 | composite (100) |
| 9.06 | 9.76 | 36-56 |
| 19.39 | 4.57 | 10-25 |
| 22.79 | 3.90 | 70-100 |

*Peaks form a composite feature.

In a further aspect, provided herein is a crystalline material (wherein part or all of a structure directing agent that is present in the material when made is removed) comprising a disordered framework of at least two ordered end member (polymorph) structures having two or more of the space groups and unit cell coordinates in Table 3:

TABLE 3

| Polymorph | Space Group | Unit Cell Coordinates [Angstroms, degrees] |
|---|---|---|
| A | Ama2 | a = 47.3, b = 17.9, c = 17.8 Å |
| B | Pc | a = 17.6, b = 45.8, c = 25.90 Å, β = 135.5° |

TABLE 3-continued

| Polymorph | Space Group | Unit Cell Coordinates [Angstroms, degrees] |
|---|---|---|
| C | P1 | a = 12.4, b = 12.4, c = 45.8 Å, α = 90.0°, β = 84.0°, γ = 89.8° |
| D | P2 | a = 12.5, b = 12.4, c = 45.7 Å, β = 84.0° |
| E | P-1 | a = 12.4, b = 12.5, c = 45.9 å, α = 84.3, β = 95.3, γ = 89.9° |
| F | P-1 | a = 12.4, b = 12.5, c = 46.1 Å, α = 83.7°, β = 95.5°, γ = 89.9° |
| G | P4$_2$/mmc | a, b = 12.58, c = 45.58 all angles identically 90° |

The ordered end member (polymorph) structures of the space groups in Table 3 exhibit one or more of the following connectivities of the tetrahedral (T) atoms of the unit cell as set forth in Table 4 to Table 9, herein.

In yet another aspect, this disclosure provides a material having the molecular formula of Formula A:

(v)X$_2$O$_3$:YO$_2$            Formula A, wherein 0≤v≤0.05 or 0.0005≤v≤0.05, X is a trivalent element, Y is a tetravalent element and O is oxygen.

In still yet another aspect, this disclosure provides methods for preparing the materials described herein.

In a further aspect, provided herein is Compound I, which is a structure directing agent (SDA) that may be used in the methods for the preparation of the as-made EMM-41. Compound I has the following structure:

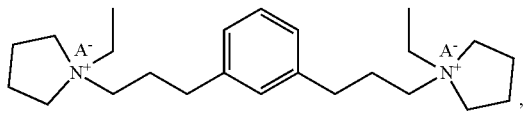

wherein A is an ion, preferably both A ions are hydroxide ions.

Yet in a further aspect, this disclosure also provides a method for preparing Compound I.

Any two or more of the features described in this specification, including in this summary section, can be combined to form combinations of features not specifically described herein. The details of one or more features are set forth in the accompanying drawings and the description below. Other features and advantages will be apparent from the description and drawings, and from the claims.

DESCRIPTION OF THE DRAWINGS

FIG. 8A and FIG. 8B each show a structural model projection of an ordered end member of polymorph F of an embodiment of the crystalline material of this invention.

DETAILED DESCRIPTION

Figure 1:
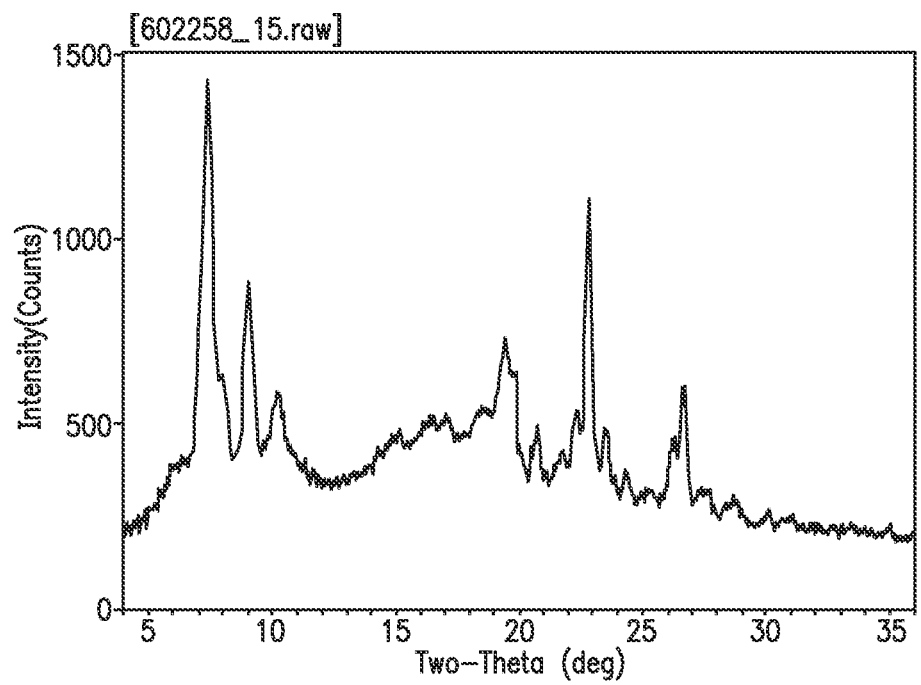
FIG. 1 shows a powder XRD pattern of an as-made EMM-41 material in accordance with Example 1.

Described herein are at least partially calcined EMM-41 crystalline materials and their characterization, for example, via electron diffraction and tetrahedral (T) atom coordination. Also described are as-made EMM-41 crystalline materials and its methods of making using a structure directing agent (SDA). The uses of EMM-41 materials are described. The structure directing agents (SDA) and the synthesis methods used to prepare them are disclosed.

The EMM-41 wherein part or all of the organic template has been removed (e.g., via thermal treatment or other treatment) is an at least partially calcined EMM-41 material. The organic template is also referred to as the structure directing agent (SDA). The at least partially calcined EMM-41 may be described as having a chemical composition of oxides of a trivalent element (e.g., X$_2$O$_3$) and oxides of a tetravalent element (e.g., YO$_2$), where these oxides can be in various molar ratios. X is a trivalent element and Y is a tetravalent element. O is oxygen. The as-made EMM-41 (i.e., before thermal treatment or other treatment to remove the SDA) may include a SDA, which is one of the reagents employed in the synthesis method for the .EMM-41 material. The as-made EMM-41 may be subjected to thermal treatment to remove part or all of the SDA. Thermal treatment (e.g., calcination) of the as-made EMM-41 typically exposes the materials to high temperatures, e.g., to 400-700° C., in an atmosphere selected from air, nitrogen, or a mixture thereof in a furnace. In another aspect, ozone treatment of the as-made EMM-41 may be used to remove part or all of the SDA. EMM-41 wherein part or all of the SDA has been removed can be used as adsorbents and catalysts or support for catalysts for hydrocarbon conversions, e.g., conversion of organic compounds to a converted product.

At Least Partially Calcined EMM-41 Materials

In one aspect, the EMM-41 material, wherein part of all of the SDA has been removed, (e.g., an at least partially calcined EMM-41 material) has at least five (5), preferably all of the XRD peaks in degree 2-theta of Table 1A:

TABLE 1A

| degrees 2-theta (±0.2) | d-spacing (Å) | relative integrated intensity [100 × I/(Io)] |
|---|---|---|
| 7.35* | 12.03 | composite |
| 7.38* | 11.97 | composite (100) |
| 9.04 | 9.78 | 20-40 |

TABLE 1A-continued

| degrees 2-theta (±0.2) | d-spacing (Å) | relative integrated intensity [100 × I/(Io)] |
|---|---|---|
| 10.28 | 8.60 | 9-20 |
| 14.39 | 6.15 | 3-10 |
| 22.77 | 3.90 | 20-40 |

*Peaks form a composite feature.

As used herein, the term "relative integrated intensity" is the relative intensity of an XRD peak which is normalized to the relative intensities of the XRD features at 7.2 to 7.4 degrees 2-theta as one composite feature having an integrated relative intensity of 100. The peaks in Table 1A at 7.35 and 7.38 degrees 2-theta form a composite feature which becomes more difficult to resolve as crystals become smaller.

In one or more aspects, the EMM-41 materials, wherein part or all of the SDA has been removed may have at least six (6), or seven (7), eight (8) or preferably all of the XRD peaks selected from Table 2 XRD peaks with the degree 2-theta and d-spacing values selected from Table 1B. The d-spacing values have a deviation determined based on the corresponding deviation ±0.20 degree 2-theta when converted to the corresponding values for d-spacing using Bragg's law:

TABLE 1B

| degrees 2-theta (±0.2) | d-spacing (Å) | relative integrated intensity [100 × I/(Io)] |
|---|---|---|
| 7.35* | 12.03 | composite |
| 7.38* | 11.97 | composite (100) |
| 8.02 | 11.01 | 5-15 |
| 9.04 | 9.78 | 20-40 |
| 10.28 | 8.60 | 9-20 |
| 14.39 | 6.15 | 3-10 |
| 22.25 | 3.99 | 4-10 |
| 22.77 | 3.90 | 20-40 |
| 26.20 | 3.40 | 5-11 |

*Peaks form a composite feature.

The XRD patterns described herein with the XRD peaks described herein use Cu(Kα) radiation.

In one or more aspects, the EMM-41 material (wherein part or all of the SDA has been removed by thermal treatment or other treatments) may have a micropore volume of at least 0.20 m²/g or in the range of 0.25 to 0.30, or 0.22 to 0.28 cc/g and/or a total BET surface area in the range of at least 495 m²/g or in the range of from 400 to 650 m²/g or 495 to 629 m²/g.

For example, the material (wherein part or all of the SDA has been removed) may have at least four (4) of the XRD peaks of Table 1A or at least six (6) of the XRD peaks in degree 2-theta selected from Table 1B and the micropore volume and/or BET surface area set forth above and/or the disordered framework of at least one polymorph structure having one or more of the space groups and unit cell coordinates set forth above.

In one or more aspects, the EMM-41 material (wherein part or all of the SDA is removed) may adsorb from or at least 60 mg (milligrams) of n-hexane per g (gram) EMM-41 material (e.g., in the range of 60 to 150 mg/g of n-hexane), based on the weight of the crystalline material, upon contact with a fluid containing the n-hexane component. This material may also be suitable for adsorbing at least 40 mg/g of 2,3-dimethylbutane (e.g., in the range of 40 to 130 mg/g of 2,3-dimethylbutane), based on the weight of the crystalline material, upon contact with a fluid containing the 2,3-dimethylbutane component. This material may also be suitable for adsorbing at least 40 mg/g of 2,2-dimethylbutane (e.g., in the range of 40 to 130 mg/g of 2,2-dimethylbutane), based on the weight of the crystalline material, upon contact with a fluid containing the 2,2-dimethylbutane component. This material may also be suitable for absorbing at least 60 mg/g of mesitylene (e.g., in the range of 60 to 90 mg/g of mesitylene), based on the weight of the crystalline material, upon contact with a fluid containing the mesitylene component.

For example, the material may adsorb in the range of 60 to 150 mg/g or 60 to 120 mg/g or 90 to 130 mg/g or 98 to 120 mg/g of n-hexane, based on the weight of the crystalline material. The material may adsorb in the range of 40 to 130 mg/g or 80 to 110 mg/g or 104 to 127 mg/g of 2,3-dimethylbutane, based on the weight of the crystalline material. The material may adsorb in the range of 40 to 130 mg/g or 80 to 110 mg/g or 75 to 91 of 2,2-dimethylbutane, based on the weight of the crystalline material. The material may also be suitable for absorbing at least 60 mg/g of mesitylene or in the range of 60 to 90 mg/g or in the range of 75 to 91 mg/g of mesitylene, based on the weight of the crystalline material.

For example, the material (wherein part or all of the SDA is removed) may have at least five (5) of the XRD peaks of Table 1A or at least six (6) XRD peaks in degree 2-theta selected from Table 1B and may adsorb at least 60 mg/g n-hexane (e.g., 60 to 150 mg/g of n-hexane or 100 mg/g of n-hexane) and/or at least 40 mg/g of 2,3-dimethylbutane (e.g., in the range of 40 to 130 mg/g of 2,3-dimethylbutane), at least 40 mg/g of 2,2-dimethylbutane (e.g., in the range of 40 to 130 mg/g of 2,2-dimethylbutane), at least 40 mg/g mesitylene (e.g., 40 to 100 mg/g of mesitylene or 60 to 90 mg/g of mesitylene), each based on the weight of the crystalline material.

In one or more aspects, the EMM-41 material (wherein part or all of the SDA is removed) may be optionally represented by the molecular formula of Formula A:

$(v)X_2O_3:YO_2$                                     Formula A, wherein $0 \leq v \leq 0.05$ or $0.0005 \leq v \leq 0.05$, X is a trivalent element, Y is a tetravalent element and O is oxygen. X may be selected from B, Al, Fe, and Ga, or a mixture thereof. For example, X may comprise or be Al or X may comprise or be B. Y may be selected from Si, Ge, Sn, Ti, and Zr, or a mixture thereof. For example, Y may comprise or be Si. The oxygens in Formula A may be replaced by carbon atoms (e.g., in the form of $CH_2$), which can come from sources of the reagents used to prepare the as-made EMM-41. The oxygens in Formula A can also be replaced by nitrogen atoms, e.g., after the SDA has been removed. Formula A can represent the framework of a typical EMM-41 material wherein part or all of the SDA has been removed, and is not meant to be the sole representation of an EMM-41 material. The EMM-41 material may contain SDA and/or impurities after appropriate treatments to remove the SDA and impurities, which are not accounted for in Formula A. Further, Formula A does not include the protons and charge compensating ions that may be present in the EMM-41 material.

The variable v represents the molar ratio relationship of $X_2O_3$ to $YO_2$ in Formula A. For example, when v is 0.0005, the molar ratio of Y to X is 1000 (e.g., the molar ratio of Si/B or Si/Al is 1000). When v is 0.05, the molar ratio of Y to X is 10 (e.g., the molar ratio of Si/B or Si/Al is 10). The molar ratio of Y to X may be 5 to 40 or 5 to 25 when X is B (e.g., the molar ratio of Si/B is 5 to 40 or 5 to 25). The molar ratio of Y to X may be 30 to infinity, or 30 to 1000, or 50 to 1000, or 100 to 1000, or 200 to 1000, or 300 to 1000, or 400 to 1000, or 500 to 1000 when X is Al (e.g., the molar ratio of Si/Al is 100 to 1000 or 500 to 1000).

Electron Diffraction and Characterization of EMM-41 Materials

Electron diffraction is one of many well-known characterization techniques for material science. The electron diffraction technique is discussed in great detail in Structural Electron Crystallography by D. L. Dorset, Plenum, N.Y., 1995, the entirety of which is incorporated herein by reference.

The composition matter of EMM-41 may be defined by its crystal structure as determined by electron diffraction. Each end polymorph of EMM-41 may be defined by a unit cell, a space group symmetry, and the atoms within the asymmetric unit of the unit cell. In one or more embodiments for the composition of matter of this invention, EMM-41, the solution of the atomic structure indicates a possible twinning, intergrowth, and/or disorder between two or more different end polymorphs.

In embodiments of this invention, the EMM-41 material (wherein part or all of the SDA is removed) is a crystalline material comprising a disordered framework of at least one polymorph structure having one or more of the space groups and unit cell coordinates shown in Table 3:

TABLE 3

| Polymorph | Space Group | Unit Cell Dimensions [Angstroms, degrees] |
|---|---|---|
| A | Ama2 | a = 47.3, b = 17.9, c = 17.8 Å |
| B | Pc | a = 17.6, b = 45.8, c = 25.90 Å, β = 135.5° |
| C | P1 | a = 12.4, b = 12.4, c = 45.8 Å, α = 90.0°, β = 84.0°, γ = 89.8° |
| D | P2 | a = 12.5, b = 12.4, c = 45.7 Å, β = 84.0° |
| E | P-1 | a = 12.4, b = 12.5, c = 45.9 å, α = 84.3, β = 95.3, γ = 89.9° |
| F | P-1 | a = 12.4, b = 12.5, c = 46.1 Å, α = 83.7°, β = 95.5°, γ = 89.9° |

In FIGS. 3 to 10, atomic models are shown of the ordered end member (polymorph) structures of the composition of matter for this invention. The unit cell determinations of the structures were made using cRED (Continuous Rotational Electron Diffraction) in combination with modeling software from Material Studios (available from BIOVIA, formerly Accelrys). Details of unit cell symmetry may be found in International Tables for Crystallography, Volume A:Space-Group Symmetry, 5$^{th}$ ed., Theo. Hahn, T, 2005.

Figure 3B:
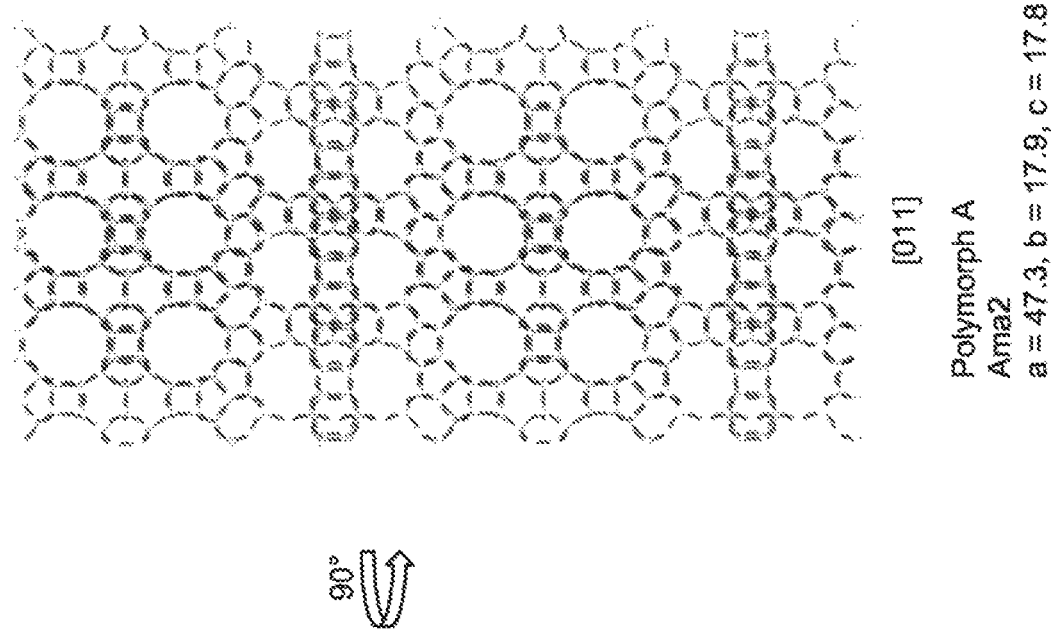
FIG. 3A and FIG. 3B each show a structural model projection of an ordered end member of polymorph A of an embodiment of the crystalline material of this invention.
Figure 3A:
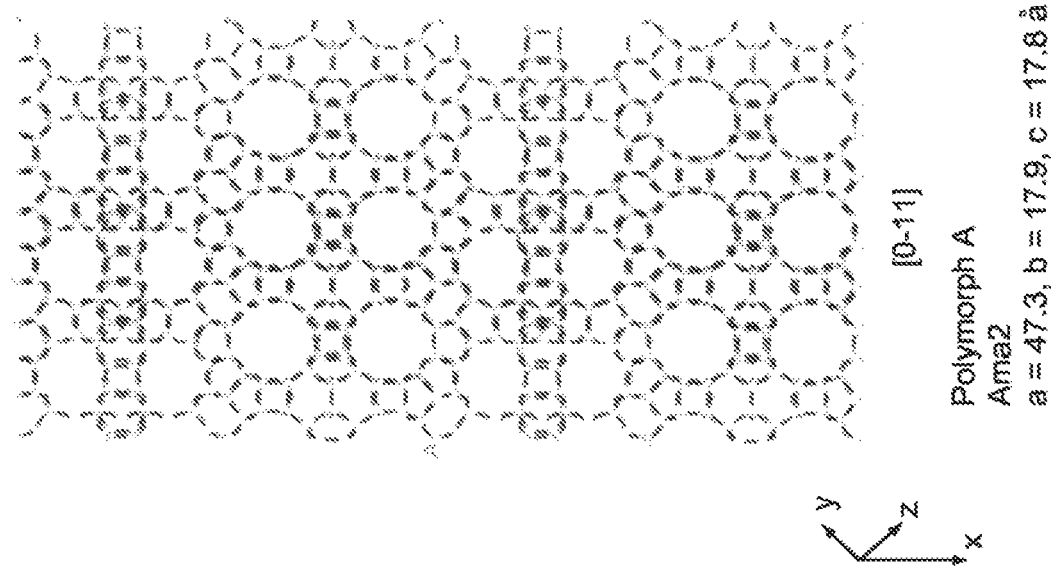

FIG. 3A shows an atomic structure model for an ordered end member of polymorph A having orthorhombic symmetry with a space group Ama and a representative unit cell of magnitude a=47.3, b=17.9, c=17.8 angstroms viewed along [0-11] and having alternating AABB structures of 10-membered and 12-membered rings, respectively.

FIG. 3B shows a model of the structure of FIG. 3A, rotated 90 degrees about the x-axis viewed along [011] and having alternating BBAA structures of 12-membered and 10-membered rings, respectively.

Figure 4A:
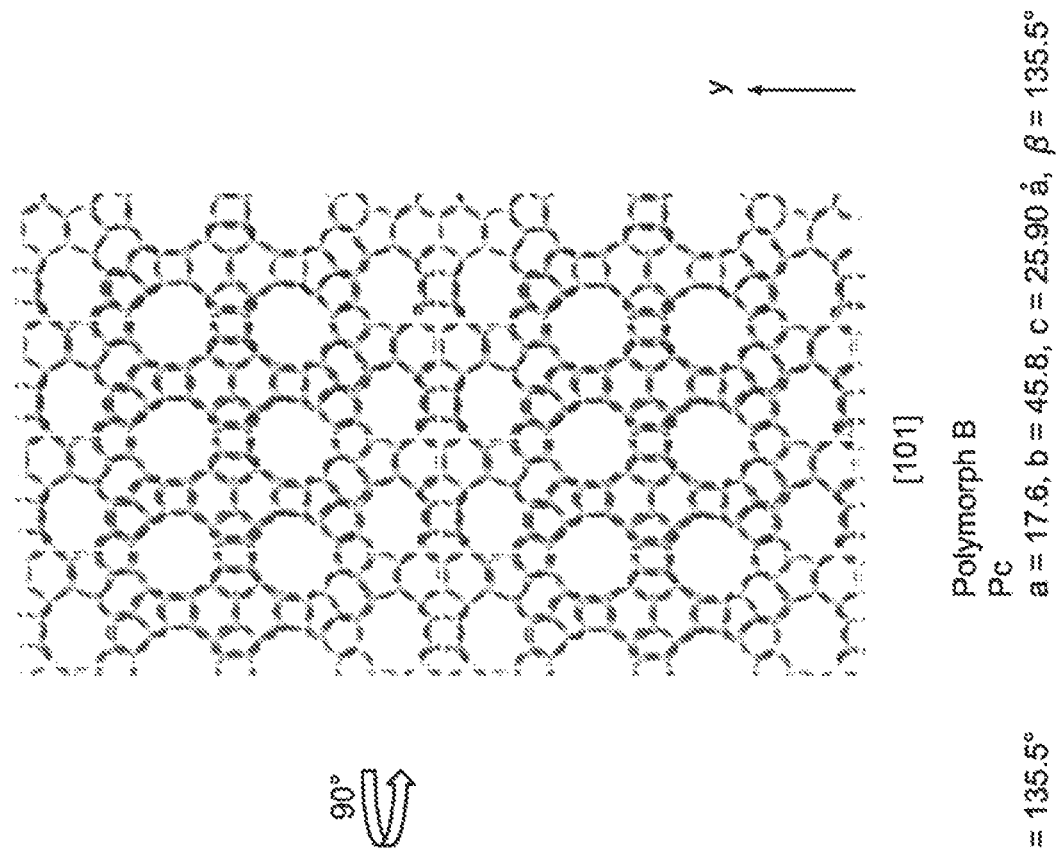
FIG. 4A and FIG. 4B each show a structural model projection of an ordered end member of polymorph B of an embodiment of the crystalline material of this invention.

FIG. 4A shows a model of an atomic structure model for an ordered end member of polymorph B having monoclinic symmetry with a space group Pc and a representative unit cell of magnitude a=17.6, b=45.8, c=25.90 angstroms and angle β=135.5 degrees viewed along [001] and having alternating BAAB structures of 10-membered and 12-membered rings, respectively.

Figure 4B:
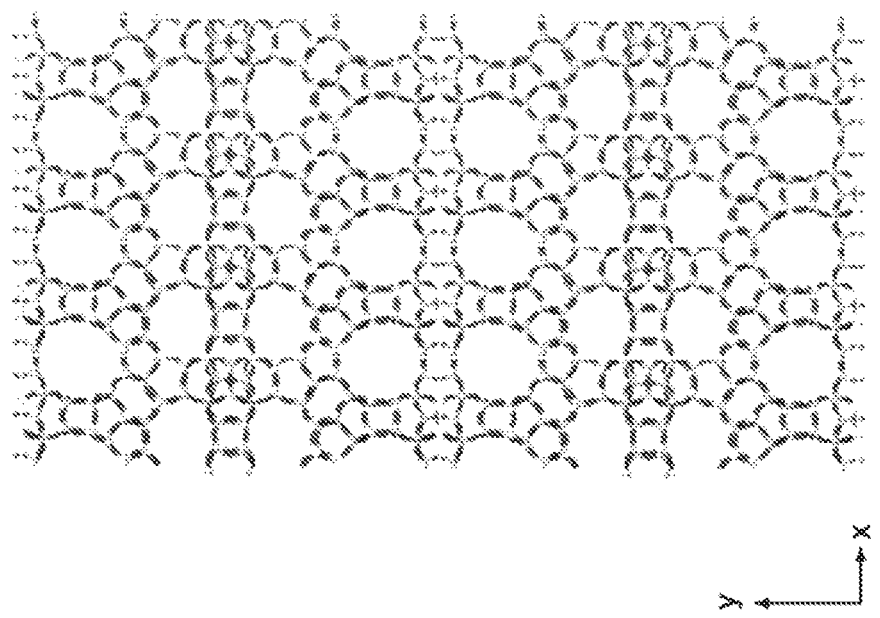

FIG. 4B shows a model of the atomic structure of FIG. 4A, rotated 90 degrees about the y-axis viewed along [101] and having alternating ABBA structures of 12-membered and 10-membered rings, respectively.

Figure 5A:
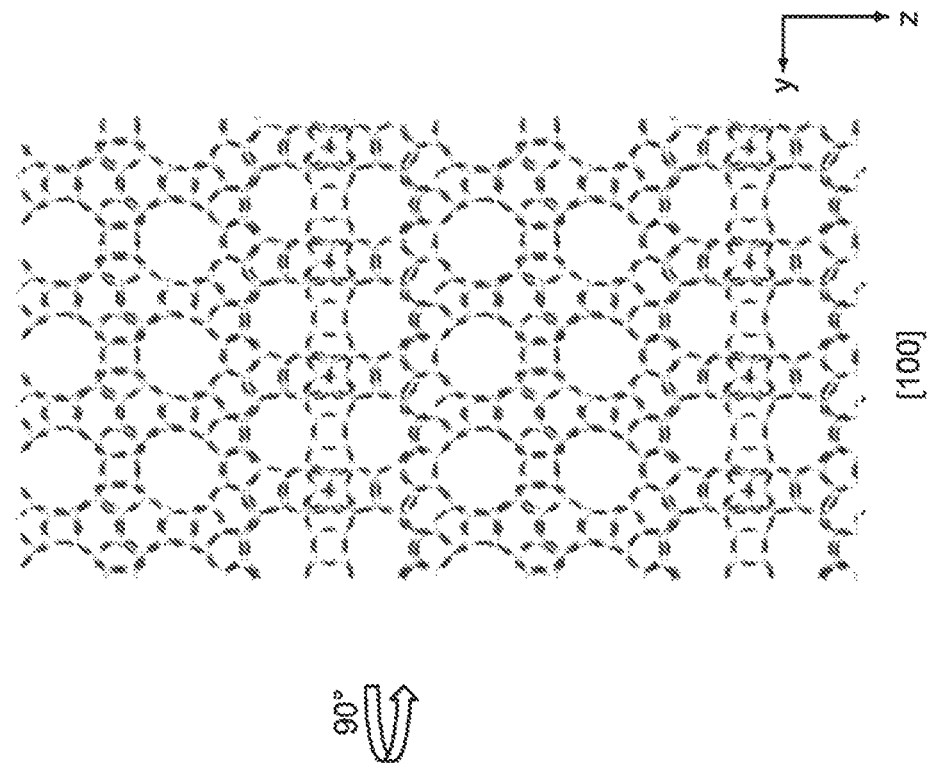
FIG. 5A and FIG. 5B each show a structural model projection of an ordered end member of polymorph C of an embodiment of the crystalline material of this invention.

FIG. 5A shows a model of an atomic structure model for an ordered end member of polymorph C having triclinic symmetry with a space group P1 and a representative unit cell of magnitude a=12.4, b=12.4, c=45.8 angstroms and angle β=84.05 and γ=89.8 degrees viewed along [010] and having alternating non-orthogonal AABB structures of 10-membered and 12-membered rings, respectively.

Figure 5B:
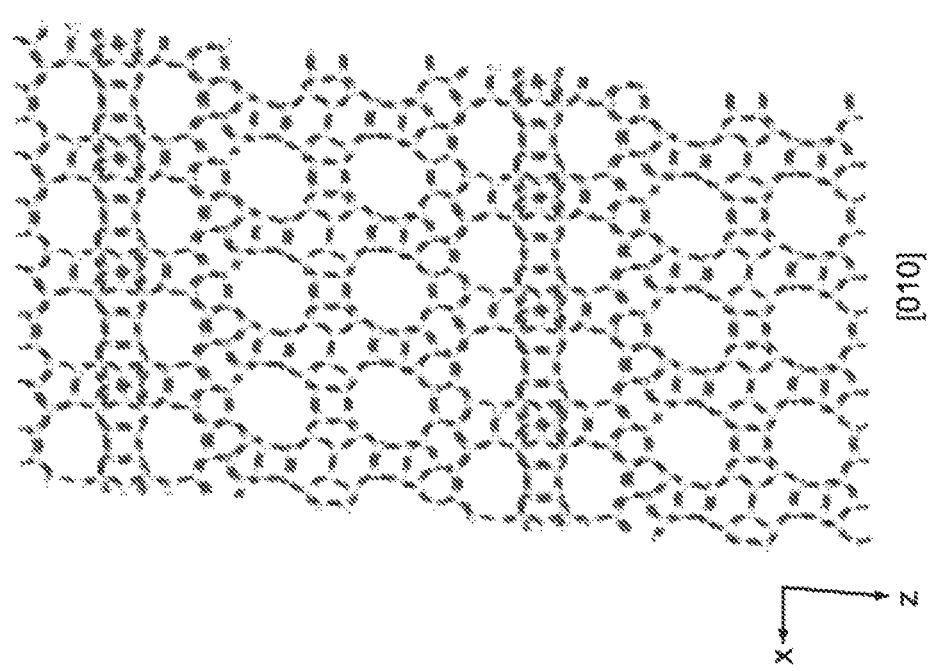

FIG. 5B shows a model of the atomic structure of FIG. 5A, rotated about the z-axis viewed along [100] and having alternating BBAA structures of 10-membered and 12-membered rings, respectively.

Figure 6A:
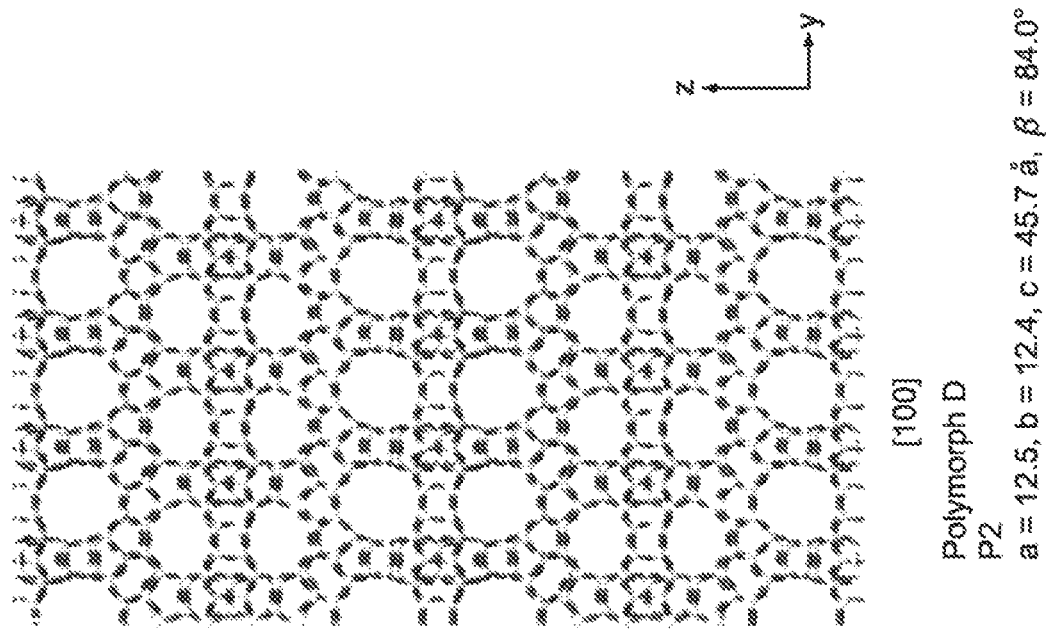
FIG. 6A and FIG. 6B each show a structural model projection of an ordered end member of polymorph D of an embodiment of the crystalline material of this invention.

FIG. 6A shows a model of an atomic structure model for an ordered end member of polymorph D having monoclinic symmetry with a space group P2 and a representative unit cell of magnitude a=12.5, b=12.4, c=45.7 angstroms and angle β=84.0 degrees viewed along [010] and having alternating non-orthogonal ABBA structures of 10-membered and 12-membered rings, respectively.

Figure 6B:
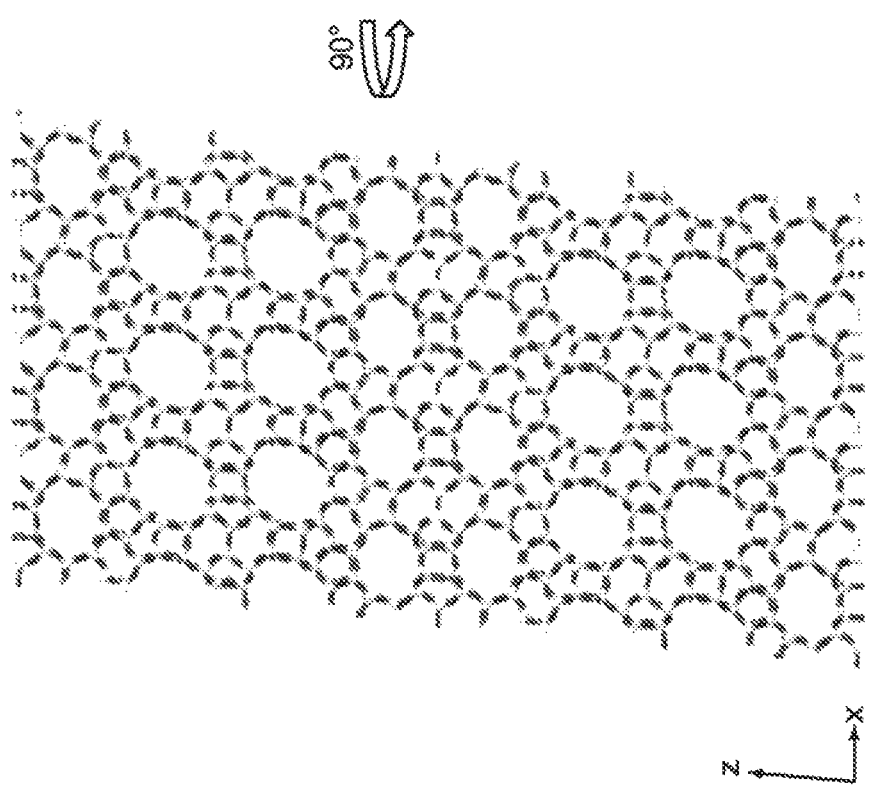

FIG. 6B shows a model of the atomic structure of FIG. 6A, rotated about the z-axis with viewed along [100] and having alternating BAAB structures of 10-membered and 12-membered rings, respectively.

Figure 7A:
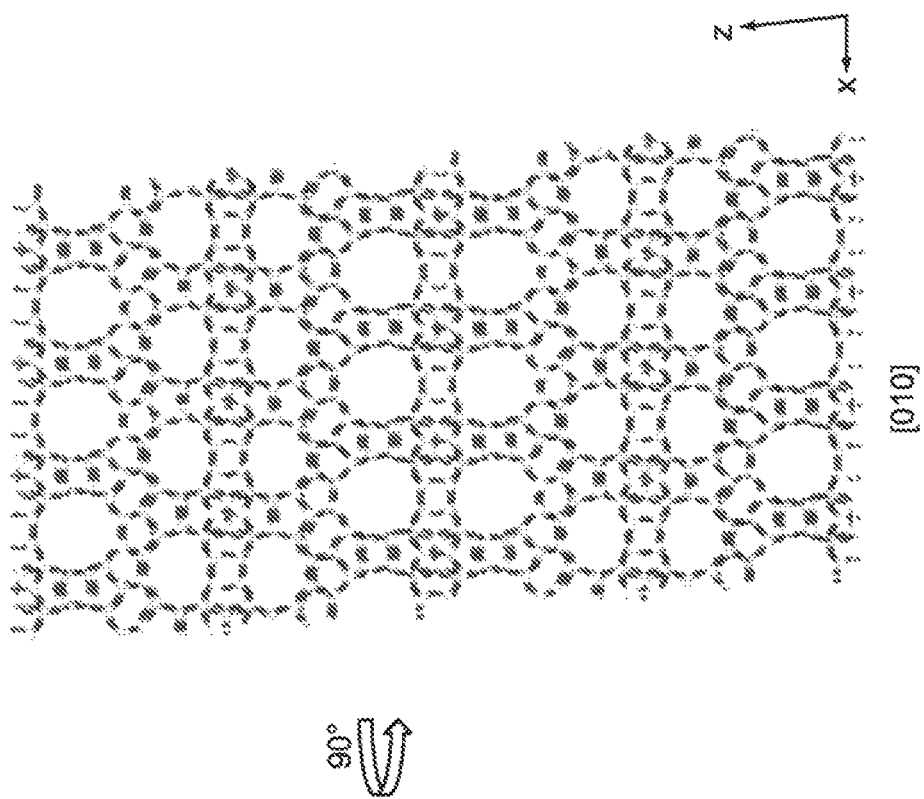
FIG. 7A and FIG. 7B each show a structural model projection of an ordered end member of polymorph E of an embodiment of the crystalline material of this invention.

FIG. 7A shows a model of an atomic structure model for an ordered end member of polymorph E having triclinic symmetry with a space group P-1 and a representative unit cell of magnitude a=12.4, b=12.5, c=45.9 angstroms and angle α=84.3, β=95.3 and γ=89.9 degrees viewed along [100] and having alternating non-orthogonal ABBA structures of 10-membered and 12-membered rings, respectively.

Figure 7B:
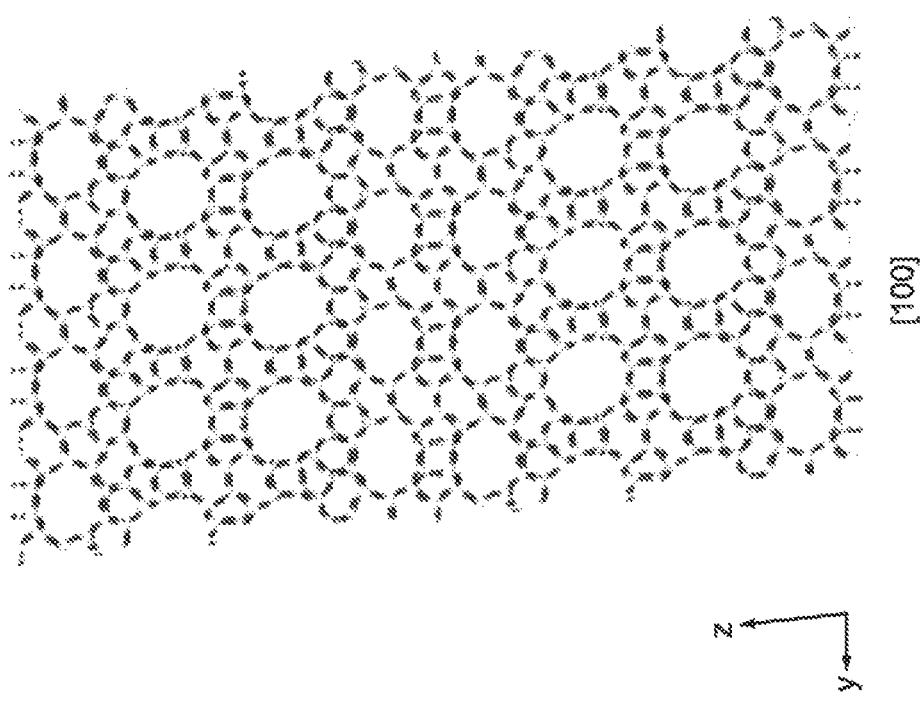

FIG. 7B shows a model of the atomic structure of FIG. 7A, rotated about the z-axis viewed along [010] and having alternating non-orthogonal BAAB structures of 10-membered and 12-membered rings, respectively.

FIG. 8A shows a model of an atomic structure model for an ordered end member of polymorph F having triclinic symmetry with a space group P-1 and a representative unit cell of magnitude a=12.4, b=12.5, c=46.1 angstroms and angle α=83.7, β=95.5 and γ=89.9 degrees viewed along [010] and having alternating non-orthogonal BAAB structures of 10-membered and 12-membered rings, respectively.

FIG. 8B shows a model of the atomic structure of FIG. 8A, rotated about the z-axis viewed along [100] and having alternating non-orthogonal ABBA structures of 10-membered and 12-membered rings, respectively.

Figure 9A:
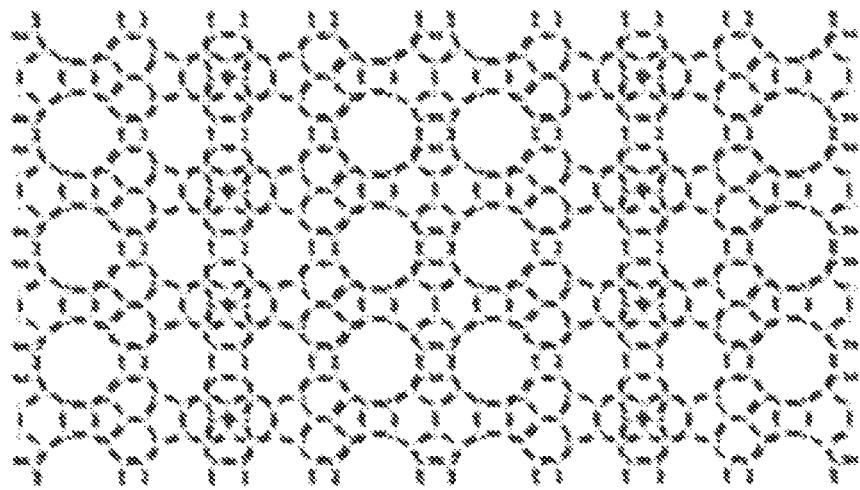
FIG. 9A and FIG. 9B each show a structural model projection of an ordered end member of polymorph G of an embodiment of the crystalline material of this invention.

FIG. 9A shows a model of an atomic structure model for an ordered end member of polymorph G having tetragonal symmetry with a space group P42/mmc and a representative unit cell of magnitude a, b=12.58, c=45.58 angstroms and angles α=β=γ=90 degrees and having alternating ABBA structures of 10-membered and 12-membered rings, respectively.

Figure 9B:
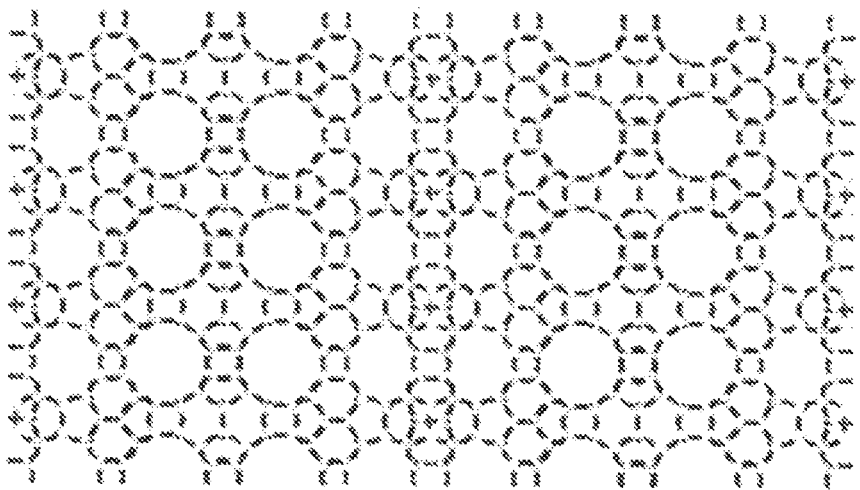

FIG. 9B shows a model of the atomic structure of FIG. 9A, rotated about the axis and having alternating BAAB structures of 10-membered and 12-membered rings, respectively.

Figure 10A:
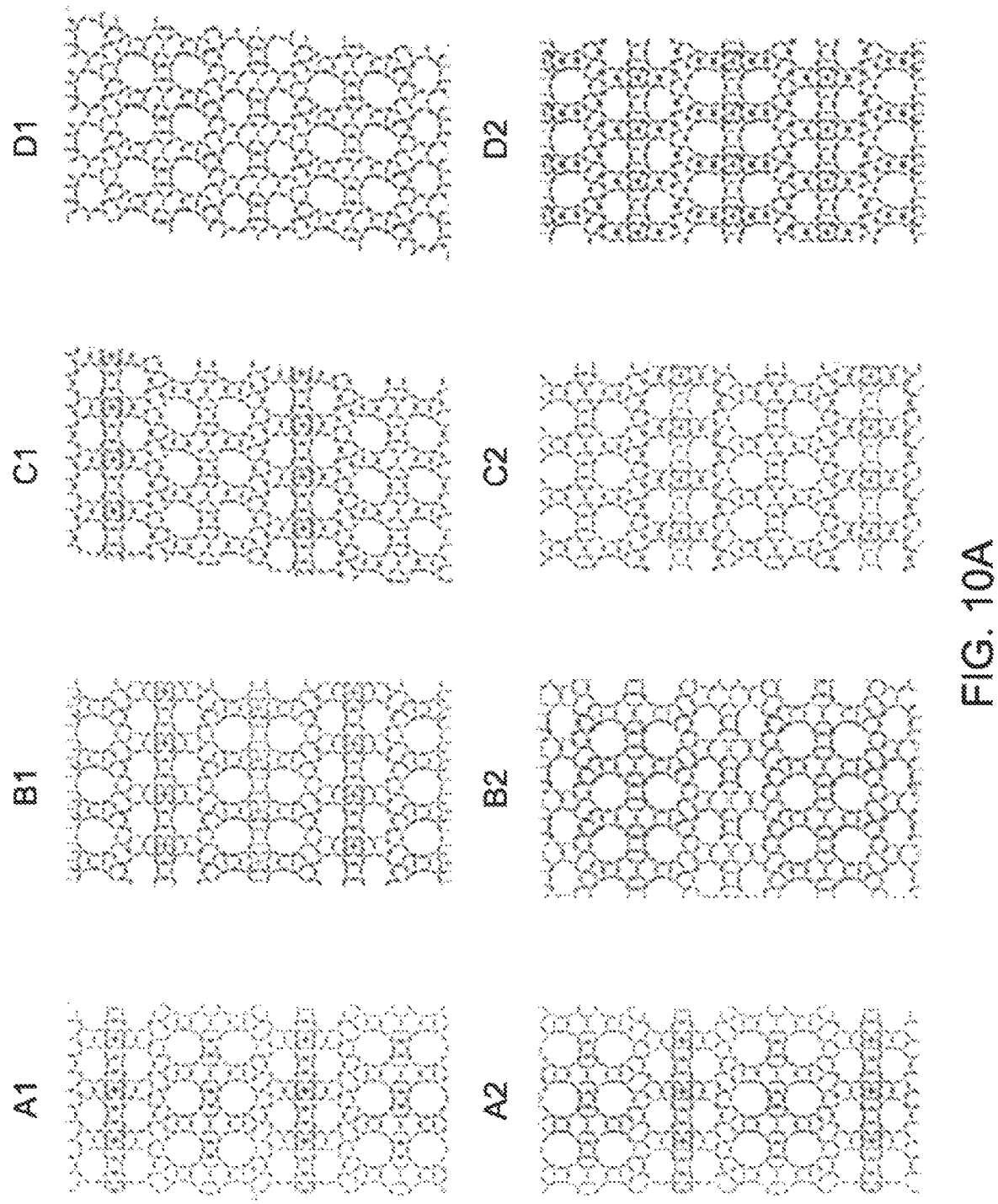
FIG. 10A shows a comparison of the structural model projections of ordered end member of polymorphs A to D of embodiments of the crystalline material of this invention.

FIG. 10A shows a comparison of the models of the atomic structures of ordered end members of polymorphs A to D of FIGS. 3A, 4A, 5A and 6A, respectively. FIG. 10A shows a comparison of the models of the atomic structures of ordered end members of polymorphs A to D of FIGS. 3B, 4B, 5B and 6B, respectively.

Figure 10B:
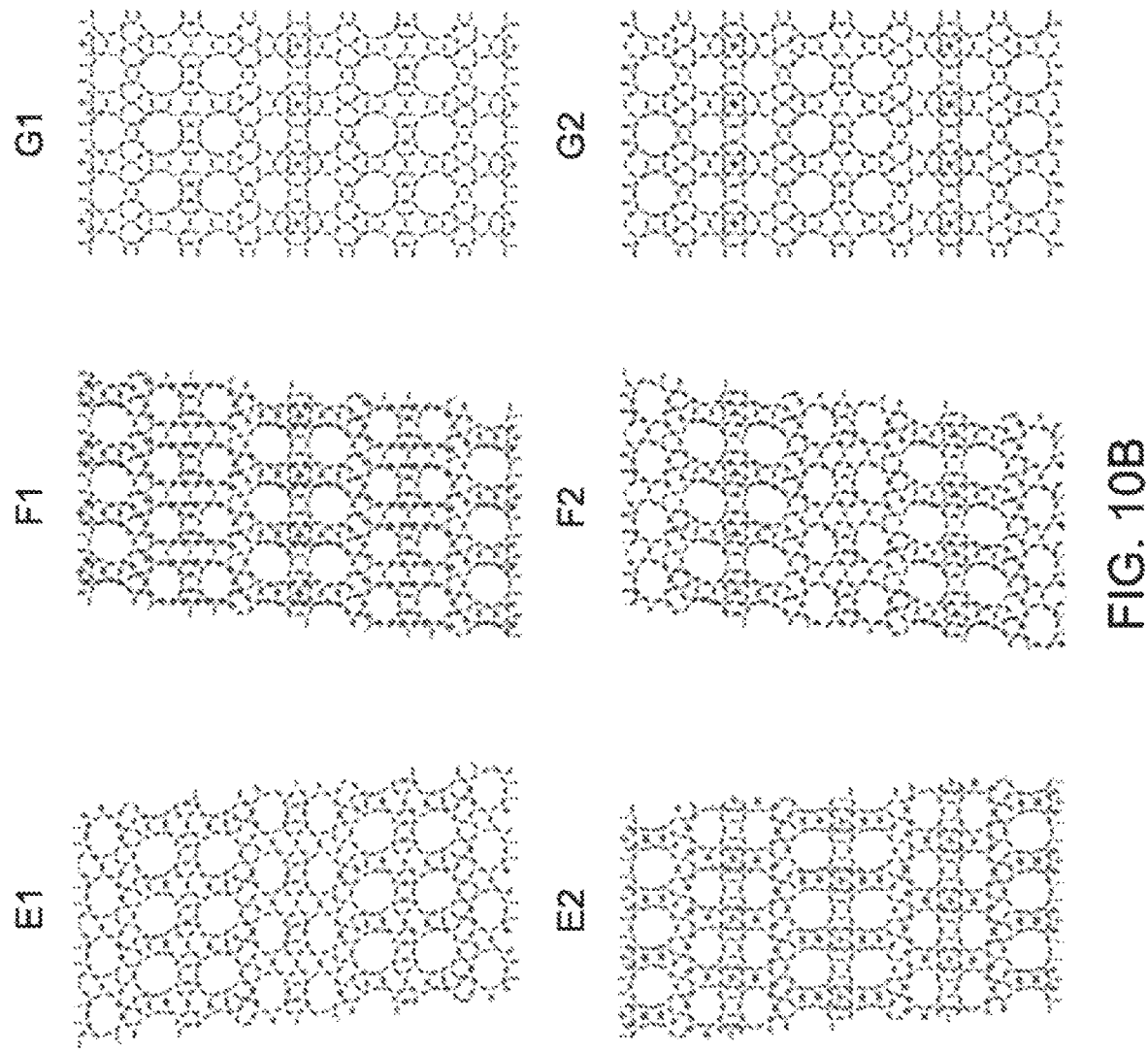
FIG. 10B shows a comparison of the structural model projections of ordered end member of polymorphs E to G of embodiments of the crystalline material of this invention.

FIG. 10B shows a comparison of the models of the atomic structures of ordered end members of polymorphs E to G of FIGS. 7A, 8A and 9A, respectively. FIG. 10B shows a comparison of the models of the atomic structures of ordered end members of polymorphs E to G of FIGS. 7B, 8B and 9B, respectively.

Tetrahedral (T) Atom Coordinates of EMM-41 Materials

The ordered end members of the polymorph structures of the space groups in Table 3 exhibit one or more of the following coordination sequences of the tetrahedral (T) atoms of the unit cell as set forth in Table 4 to Table 10, below. Coordination sequences are defined in the Atlas of Zeolite Structures.

TABLE 4

Polymorph A in Ama2 Space Group

| T atom | Coordination Sequence |
| --- | --- |
| T1 | 4, 11, 20, 29, 47, 82, 117, 141, 165, 217 |
| T2 | 4, 12, 24, 33, 53, 85, 121, 144, 174, 222 |
| T3 | 4, 10, 21, 36, 56, 80, 107, 144, 193, 232 |
| T4 | 4, 11, 22, 37, 56, 81, 110, 146, 185, 227 |
| T5 | 4, 12, 18, 33, 52, 80, 110, 141, 179, 227 |
| T6 | 4, 12, 18, 34, 58, 82, 109, 136, 185, 229 |
| T7 | 4, 10, 21, 36, 56, 78, 108, 146, 190, 226 |
| T8 | 4, 9, 18, 33, 55, 81, 108, 142, 181, 220 |
| T9 | 4, 9, 18, 33, 55, 81, 108, 142, 183, 222 |
| T10 | 4, 12, 21, 36, 54, 80, 113, 147, 177, 221 |
| T11 | 4, 11, 23, 35, 54, 80, 113, 146, 176, 215 |
| T12 | 4, 11, 20, 29, 47, 82, 117, 141, 165, 217 |
| T13 | 4, 10, 21, 36, 56, 80, 105, 143, 194, 228 |
| T14 | 4, 11, 22, 37, 56, 79, 108, 147, 185, 227 |
| T15 | 4, 12, 18, 33, 52, 80, 110, 138, 175, 227 |
| T16 | 4, 12, 19, 35, 57, 78, 110, 140, 184, 226 |
| T17 | 4, 11, 24, 37, 51, 81, 116, 148, 172, 213 |
| T18 | 4, 10, 21, 36, 56, 78, 106, 145, 190, 224 |
| T19 | 4, 9, 18, 33, 55, 81, 108, 142, 181, 220 |
| T20 | 4, 12, 22, 33, 55, 84, 120, 146, 170, 221 |
| T21 | 4, 9, 18, 33, 55, 81, 108, 142, 183, 222 |
| T22 | 4, 12, 20, 34, 55, 82, 112, 143, 178, 222 |
| T23 | 4, 11, 21, 36, 54, 80, 110, 144, 180, 217 |
| T24 | 4, 11, 20, 35, 58, 80, 104, 143, 191, 236 |
| T25 | 4, 12, 18, 33, 52, 80, 112, 143, 177, 227 |
| T26 | 4, 11, 20, 35, 58, 78, 103, 144, 191, 229 |
| T27 | 4, 12, 18, 33, 52, 80, 112, 140, 174, 226 |
| T28 | 4, 12, 21, 32, 55, 89, 109, 140, 174, 232 |
| T29 | 4, 12, 20, 33, 54, 82, 116, 142, 174, 215 |
| T30 | 4, 11, 20, 30, 47, 76, 113, 145, 178, 216 |
| T31 | 4, 11, 20, 30, 47, 76, 113, 149, 178, 208 |
| T32 | 4, 11, 20, 30, 47, 76, 113, 149, 172, 208 |
| T33 | 4, 11, 20, 30, 47, 76, 113, 145, 172, 214 |
| T34 | 4, 12, 19, 35, 51, 87, 124, 140, 166, 214 |

TABLE 5

Polymorph B in Pc Space Group

| T atom | Coordination Sequence |
| --- | --- |
| T1 | 4, 11, 20, 30, 46, 77, 115, 147, 171, 210 |
| T2 | 4, 12, 24, 33, 53, 85, 119, 141, 175, 223 |
| T3 | 4, 10, 21, 36, 56, 78, 108, 146, 189, 227 |
| T4 | 4, 11, 22, 37, 56, 81, 112, 149, 186, 224 |
| T5 | 4, 12, 18, 33, 52, 80, 109, 138, 176, 227 |
| T6 | 4, 12, 18, 35, 59, 83, 110, 137, 189, 229 |
| T7 | 4, 10, 21, 36, 56, 78, 106, 145, 189, 225 |
| T8 | 4, 9, 18, 33, 55, 81, 108, 143, 182, 219 |
| T9 | 4, 9, 18, 33, 55, 81, 108, 143, 182, 219 |
| T10 | 4, 12, 21, 36, 53, 77, 111, 148, 176, 218 |
| T11 | 4, 11, 23, 35, 54, 80, 113, 146, 176, 216 |
| T12 | 4, 11, 20, 29, 47, 82, 117, 141, 165, 218 |
| T13 | 4, 10, 21, 36, 56, 80, 105, 145, 196, 224 |
| T14 | 4, 11, 22, 37, 56, 79, 108, 147, 185, 227 |
| T15 | 4, 12, 18, 33, 52, 80, 110, 138, 175, 227 |
| T16 | 4, 12, 19, 35, 57, 79, 112, 139, 181, 227 |
| T17 | 4, 10, 21, 36, 56, 78, 106, 145, 190, 224 |
| T18 | 4, 9, 18, 33, 55, 81, 108, 142, 181, 220 |

TABLE 5-continued

Polymorph B in Pc Space Group

| T atom | Coordination Sequence |
| --- | --- |
| T19 | 4, 12, 22, 33, 54, 81, 118, 147, 169, 218 |
| T20 | 4, 9, 18, 33, 55, 81, 108, 142, 183, 220 |
| T21 | 4, 12, 20, 34, 55, 82, 112, 143, 178, 222 |
| T22 | 4, 11, 20, 35, 58, 80, 106, 146, 192, 233 |
| T23 | 4, 12, 18, 33, 52, 80, 109, 140, 180, 228 |
| T24 | 4, 11, 20, 35, 58, 78, 105, 147, 192, 226 |
| T25 | 4, 12, 18, 33, 52, 80, 112, 142, 178, 225 |
| T26 | 4, 12, 21, 32, 55, 89, 107, 139, 175, 233 |
| T27 | 4, 12, 20, 33, 53, 79, 112, 141, 175, 210 |
| T28 | 4, 11, 20, 30, 46, 77, 115, 147, 171, 210 |
| T29 | 4, 12, 24, 33, 53, 85, 119, 141, 175, 223 |
| T30 | 4, 10, 21, 36, 56, 78, 108, 146, 189, 227 |
| T31 | 4, 11, 22, 37, 56, 81, 112, 149, 186, 224 |
| T32 | 4, 12, 18, 33, 52, 80, 109, 138, 176, 227 |
| T33 | 4, 12, 18, 35, 59, 83, 110, 137, 189, 229 |
| T34 | 4, 10, 21, 36, 56, 78, 106, 145, 189, 225 |
| T35 | 4, 9, 18, 33, 55, 81, 108, 143, 182, 219 |
| T36 | 4, 9, 18, 33, 55, 81, 108, 143, 182, 219 |
| T37 | 4, 12, 21, 36, 53, 77, 111, 148, 176, 218 |
| T38 | 4, 11, 23, 35, 54, 80, 113, 146, 176, 216 |
| T39 | 4, 11, 20, 29, 47, 82, 117, 141, 165, 218 |
| T40 | 4, 10, 21, 36, 56, 80, 105, 145, 196, 224 |
| T41 | 4, 11, 22, 37, 56, 79, 108, 147, 185, 227 |
| T42 | 4, 12, 18, 33, 52, 80, 110, 138, 175, 227 |
| T43 | 4, 12, 19, 35, 57, 79, 112, 139, 181, 227 |
| T44 | 4, 10, 21, 36, 56, 78, 106, 145, 190, 224 |
| T45 | 4, 9, 18, 33, 55, 81, 108, 142, 181, 220 |
| T46 | 4, 12, 22, 33, 54, 81, 118, 147, 169, 218 |
| T47 | 4, 9, 18, 33, 55, 81, 108, 142, 183, 220 |
| T48 | 4, 12, 20, 34, 55, 82, 112, 143, 178, 222 |
| T49 | 4, 11, 20, 35, 58, 80, 106, 146, 192, 233 |
| T50 | 4, 12, 18, 33, 52, 80, 109, 140, 180, 228 |
| T51 | 4, 11, 20, 35, 58, 78, 105, 147, 192, 226 |
| T52 | 4, 12, 18, 33, 52, 80, 112, 142, 178, 225 |
| T53 | 4, 12, 21, 32, 55, 89, 107, 139, 175, 233 |
| T54 | 4, 12, 20, 33, 53, 79, 112, 141, 175, 210 |
| T55 | 4, 11, 20, 29, 47, 82, 117, 141, 165, 215 |
| T56 | 4, 12, 24, 33, 52, 82, 119, 145, 173, 219 |
| T57 | 4, 10, 21, 36, 56, 80, 107, 144, 193, 232 |
| T58 | 4, 11, 22, 37, 56, 81, 108, 144, 189, 227 |
| T59 | 4, 12, 18, 33, 52, 80, 110, 141, 177, 225 |
| T60 | 4, 12, 18, 34, 58, 82, 109, 136, 185, 229 |
| T61 | 4, 10, 21, 36, 56, 78, 108, 144, 188, 230 |
| T62 | 4, 9, 18, 33, 55, 81, 108, 142, 181, 222 |
| T63 | 4, 9, 18, 33, 55, 81, 108, 142, 183, 222 |
| T64 | 4, 12, 21, 36, 54, 81, 115, 146, 174, 222 |
| T65 | 4, 11, 23, 35, 55, 83, 115, 145, 176, 222 |
| T66 | 4, 11, 20, 30, 46, 77, 115, 147, 168, 210 |
| T67 | 4, 10, 21, 36, 56, 80, 105, 143, 193, 228 |
| T68 | 4, 11, 22, 37, 56, 79, 110, 150, 186, 224 |
| T69 | 4, 12, 18, 33, 52, 80, 112, 140, 174, 225 |
| T70 | 4, 12, 19, 36, 58, 79, 111, 141, 188, 226 |
| T71 | 4, 9, 18, 33, 55, 81, 108, 143, 184, 221 |
| T72 | 4, 12, 22, 33, 55, 82, 116, 146, 172, 219 |
| T73 | 4, 9, 18, 33, 55, 81, 108, 143, 184, 221 |
| T74 | 4, 12, 20, 34, 54, 79, 110, 144, 177, 219 |
| T75 | 4, 11, 20, 35, 58, 80, 104, 143, 191, 232 |
| T76 | 4, 12, 18, 33, 52, 80, 112, 143, 177, 227 |
| T77 | 4, 11, 20, 35, 58, 105, 146, 187, 227 |
| T78 | 4, 12, 18, 33, 52, 80, 112, 140, 176, 228 |
| T79 | 4, 12, 21, 32, 55, 89, 109, 140, 174, 233 |
| T80 | 4, 12, 20, 33, 54, 82, 116, 142, 174, 216 |
| T81 | 4, 11, 20, 29, 47, 82, 117, 141, 165, 215 |
| T82 | 4, 12, 24, 33, 52, 82, 119, 145, 173, 219 |
| T83 | 4, 10, 21, 36, 56, 80, 107, 144, 193, 232 |
| T84 | 4, 11, 22, 37, 56, 81, 108, 144, 189, 227 |
| T85 | 4, 12, 18, 33, 52, 80, 110, 141, 177, 225 |
| T86 | 4, 12, 18, 34, 58, 82, 109, 136, 185, 229 |
| T87 | 4, 10, 21, 36, 56, 78, 108, 144, 188, 230 |
| T88 | 4, 9, 18, 33, 55, 81, 108, 142, 181, 222 |
| T89 | 4, 9, 18, 33, 55, 81, 108, 142, 183, 222 |
| T90 | 4, 12, 21, 36, 54, 81, 115, 146, 174, 222 |
| T91 | 4, 11, 23, 35, 55, 83, 115, 145, 176, 222 |
| T92 | 4, 11, 20, 30, 46, 77, 115, 147, 168, 210 |
| T93 | 4, 10, 21, 36, 56, 80, 105, 143, 193, 228 |
| T94 | 4, 11, 22, 37, 56, 79, 110, 150, 186, 224 |

TABLE 5-continued

Polymorph B in Pc Space Group

| T atom | Coordination Sequence |
|---|---|
| T95 | 4, 12, 18, 33, 52, 80, 112, 140, 174, 225 |
| T96 | 4, 12, 19, 36, 58, 79, 111, 141, 188, 226 |
| T97 | 4, 9, 18, 33, 55, 81, 108, 143, 184, 221 |
| T98 | 4, 12, 22, 33, 55, 82, 116, 146, 172, 219 |
| T99 | 4, 9, 18, 33, 55, 81, 108, 143, 184, 221 |
| T100 | 4, 12, 20, 34, 54, 79, 110, 144, 177, 219 |
| T101 | 4, 11, 20, 35, 58, 80, 104, 143, 191, 232 |
| T102 | 4, 12, 18, 33, 52, 80, 112, 143, 177, 227 |
| T103 | 4, 11, 20, 35, 58, 78, 105, 146, 187, 227 |
| T104 | 4, 12, 18, 33, 52, 80, 112, 140, 176, 228 |
| T105 | 4, 12, 21, 32, 55, 89, 109, 140, 174, 233 |
| T106 | 4, 12, 20, 33, 54, 82, 116, 142, 174, 216 |
| T107 | 4, 10, 21, 36, 56, 80, 107, 144, 192, 232 |
| T108 | 4, 10, 21, 36, 56, 80, 107, 144, 192, 232 |
| T109 | 4, 11, 24, 37, 52, 84, 118, 147, 172, 220 |
| T110 | 4, 11, 21, 36, 54, 80, 110, 144, 180, 218 |
| T111 | 4, 11, 24, 37, 52, 84, 118, 147, 172, 220 |
| T112 | 4, 11, 21, 36, 54, 80, 110, 144, 180, 218 |
| T113 | 4, 11, 20, 30, 47, 76, 113, 141, 172, 218 |
| T114 | 4, 11, 20, 30, 47, 76, 113, 141, 176, 222 |
| T115 | 4, 11, 20, 30, 47, 76, 113, 147, 174, 214 |
| T116 | 4, 11, 20, 30, 47, 76, 113, 145, 178, 212 |
| T117 | 4, 11, 20, 30, 47, 76, 113, 149, 178, 208 |
| T118 | 4, 11, 20, 30, 47, 76, 113, 149, 172, 212 |
| T119 | 4, 11, 20, 30, 47, 76, 113, 145, 172, 214 |
| T120 | 4, 11, 20, 30, 47, 76, 113, 147, 170, 210 |
| T121 | 4, 12, 19, 35, 50, 84, 120, 139, 167, 209 |
| T122 | 4, 12, 19, 35, 50, 84, 120, 139, 167, 209 |

TABLE 6

Polymorph C in P1 Space Group

| T atom | Coordination Sequence |
|---|---|
| T1 | 4, 11, 20, 29, 47, 82, 117, 141, 165, 217 |
| T2 | 4, 12, 24, 33, 53, 85, 121, 144, 174, 222 |
| T3 | 4, 10, 21, 36, 56, 80, 107, 144, 191, 232 |
| T4 | 4, 11, 22, 37, 56, 81, 110, 146, 185, 229 |
| T5 | 4, 12, 18, 33, 52, 80, 110, 143, 181, 226 |
| T6 | 4, 12, 18, 34, 58, 82, 109, 136, 185, 229 |
| T7 | 4, 10, 21, 36, 56, 78, 108, 146, 192, 226 |
| T8 | 4, 9, 18, 33, 55, 81, 108, 142, 181, 222 |
| T9 | 4, 9, 18, 33, 55, 81, 108, 142, 183, 220 |
| T10 | 4, 12, 21, 36, 54, 80, 113, 147, 177, 221 |
| T11 | 4, 11, 23, 35, 54, 80, 113, 146, 176, 215 |
| T12 | 4, 11, 20, 29, 47, 82, 117, 141, 165, 217 |
| T13 | 4, 10, 21, 36, 56, 80, 107, 144, 193, 230 |
| T14 | 4, 11, 22, 37, 56, 81, 110, 146, 185, 227 |
| T15 | 4, 12, 18, 33, 52, 80, 110, 141, 177, 227 |
| T16 | 4, 12, 18, 34, 58, 82, 109, 136, 185, 229 |
| T17 | 4, 10, 21, 36, 56, 78, 108, 146, 190, 224 |
| T18 | 4, 9, 18, 33, 55, 81, 108, 142, 181, 220 |
| T19 | 4, 12, 20, 34, 55, 82, 112, 143, 178, 222 |
| T20 | 4, 9, 18, 33, 55, 81, 108, 142, 183, 222 |
| T21 | 4, 12, 21, 36, 54, 80, 113, 147, 177, 221 |
| T22 | 4, 11, 20, 35, 58, 80, 104, 143, 191, 234 |
| T23 | 4, 12, 18, 33, 52, 80, 112, 141, 175, 228 |
| T24 | 4, 11, 20, 35, 58, 78, 103, 144, 191, 227 |
| T25 | 4, 12, 18, 33, 52, 80, 112, 138, 172, 228 |
| T26 | 4, 12, 21, 32, 55, 89, 109, 140, 174, 232 |
| T27 | 4, 12, 20, 33, 54, 82, 116, 142, 174, 215 |
| T28 | 4, 11, 20, 29, 47, 82, 117, 141, 165, 217 |
| T29 | 4, 12, 24, 33, 53, 85, 121, 144, 174, 222 |
| T30 | 4, 10, 21, 36, 56, 80, 107, 144, 193, 230 |
| T31 | 4, 11, 22, 37, 56, 81, 110, 146, 185, 227 |
| T32 | 4, 12, 18, 33, 52, 80, 110, 141, 177, 227 |
| T33 | 4, 12, 18, 34, 58, 82, 109, 136, 185, 229 |
| T34 | 4, 10, 21, 36, 56, 78, 108, 146, 190, 224 |
| T35 | 4, 9, 18, 33, 55, 81, 108, 142, 181, 220 |
| T36 | 4, 9, 18, 33, 55, 81, 108, 142, 183, 222 |
| T37 | 4, 12, 21, 36, 54, 80, 113, 147, 177, 221 |
| T38 | 4, 11, 23, 35, 54, 80, 113, 146, 176, 215 |

TABLE 6-continued

Polymorph C in P1 Space Group

| T atom | Coordination Sequence |
|---|---|
| T39 | 4, 11, 20, 29, 47, 82, 117, 141, 165, 217 |
| T40 | 4, 10, 21, 36, 56, 78, 106, 145, 192, 224 |
| T41 | 4, 11, 20, 35, 58, 78, 103, 144, 191, 227 |
| T42 | 4, 12, 18, 33, 52, 80, 112, 138, 172, 228 |
| T43 | 4, 12, 19, 35, 57, 78, 110, 140, 184, 226 |
| T44 | 4, 10, 21, 36, 56, 80, 105, 143, 192, 228 |
| T45 | 4, 9, 18, 33, 55, 81, 108, 142, 183, 220 |
| T46 | 4, 12, 24, 33, 53, 85, 121, 144, 174, 222 |
| T47 | 4, 9, 18, 33, 55, 81, 108, 142, 181, 222 |
| T48 | 4, 12, 22, 33, 55, 84, 120, 146, 170, 221 |
| T49 | 4, 11, 20, 35, 58, 80, 104, 143, 191, 236 |
| T50 | 4, 12, 18, 33, 52, 80, 112, 143, 175, 226 |
| T51 | 4, 11, 20, 35, 58, 78, 103, 144, 191, 229 |
| T52 | 4, 12, 18, 33, 52, 80, 112, 140, 176, 227 |
| T53 | 4, 12, 21, 32, 55, 89, 109, 140, 174, 232 |
| T54 | 4, 12, 20, 33, 54, 82, 116, 142, 174, 215 |
| T55 | 4, 11, 20, 29, 47, 82, 117, 141, 165, 217 |
| T56 | 4, 12, 21, 36, 54, 80, 113, 147, 177, 221 |
| T57 | 4, 10, 21, 36, 56, 80, 105, 143, 194, 230 |
| T58 | 4, 11, 22, 37, 56, 79, 108, 147, 185, 227 |
| T59 | 4, 12, 18, 33, 52, 80, 110, 138, 177, 227 |
| T60 | 4, 12, 19, 35, 57, 78, 110, 140, 184, 226 |
| T61 | 4, 10, 21, 36, 56, 78, 106, 145, 190, 226 |
| T62 | 4, 9, 18, 33, 55, 81, 108, 142, 181, 220 |
| T63 | 4, 9, 18, 33, 55, 81, 108, 142, 183, 222 |
| T64 | 4, 12, 20, 34, 55, 82, 112, 143, 178, 222 |
| T65 | 4, 11, 21, 36, 54, 80, 110, 144, 180, 217 |
| T66 | 4, 11, 20, 29, 47, 82, 117, 141, 165, 217 |
| T67 | 4, 10, 21, 36, 56, 80, 105, 143, 192, 228 |
| T68 | 4, 11, 22, 37, 56, 79, 108, 147, 185, 229 |
| T69 | 4, 12, 18, 33, 52, 80, 110, 140, 177, 225 |
| T70 | 4, 12, 19, 35, 57, 78, 110, 140, 184, 226 |
| T71 | 4, 10, 21, 36, 56, 78, 106, 145, 192, 224 |
| T72 | 4, 9, 18, 33, 55, 81, 108, 142, 181, 222 |
| T73 | 4, 12, 22, 33, 55, 84, 120, 146, 170, 221 |
| T74 | 4, 9, 18, 33, 55, 81, 108, 142, 183, 220 |
| T75 | 4, 12, 20, 34, 55, 82, 112, 143, 178, 222 |
| T76 | 4, 11, 20, 35, 58, 78, 103, 144, 191, 229 |
| T77 | 4, 12, 18, 33, 52, 80, 112, 140, 176, 227 |
| T78 | 4, 11, 20, 35, 58, 80, 104, 143, 191, 236 |
| T79 | 4, 12, 18, 33, 52, 80, 112, 143, 175, 226 |
| T80 | 4, 12, 21, 32, 55, 89, 109, 140, 174, 232 |
| T81 | 4, 12, 20, 33, 54, 82, 116, 142, 174, 215 |
| T82 | 4, 11, 20, 29, 47, 82, 117, 141, 165, 217 |
| T83 | 4, 12, 22, 33, 55, 84, 120, 146, 170, 221 |
| T84 | 4, 10, 21, 36, 56, 78, 108, 146, 192, 226 |
| T85 | 4, 11, 20, 35, 58, 80, 104, 143, 191, 234 |
| T86 | 4, 12, 18, 33, 52, 80, 112, 141, 175, 228 |
| T87 | 4, 12, 18, 34, 58, 82, 109, 136, 185, 229 |
| T88 | 4, 10, 21, 36, 56, 80, 107, 144, 191, 232 |
| T89 | 4, 9, 18, 33, 55, 81, 108, 142, 183, 220 |
| T90 | 4, 9, 18, 33, 55, 81, 108, 142, 181, 222 |
| T91 | 4, 12, 24, 33, 53, 85, 121, 144, 174, 222 |
| T92 | 4, 11, 24, 37, 51, 81, 116, 148, 172, 213 |
| T93 | 4, 11, 20, 29, 47, 82, 117, 141, 165, 217 |
| T94 | 4, 10, 21, 36, 56, 80, 105, 143, 194, 230 |
| T95 | 4, 11, 22, 37, 56, 79, 108, 147, 185, 227 |
| T96 | 4, 12, 18, 33, 52, 80, 110, 138, 177, 227 |
| T97 | 4, 12, 19, 35, 57, 78, 110, 140, 184, 226 |
| T98 | 4, 10, 21, 36, 56, 78, 106, 145, 190, 226 |
| T99 | 4, 9, 18, 33, 55, 81, 108, 142, 181, 220 |
| T100 | 4, 12, 22, 33, 55, 84, 120, 146, 170, 221 |
| T101 | 4, 9, 18, 33, 55, 81, 108, 142, 183, 222 |
| T102 | 4, 12, 20, 34, 55, 82, 112, 143, 178, 222 |
| T103 | 4, 11, 22, 37, 56, 81, 110, 146, 185, 229 |
| T104 | 4, 12, 18, 33, 52, 80, 110, 143, 181, 226 |
| T105 | 4, 11, 22, 37, 56, 79, 108, 147, 185, 229 |
| T106 | 4, 12, 18, 33, 52, 80, 110, 140, 177, 225 |
| T107 | 4, 12, 20, 33, 54, 82, 116, 142, 174, 215 |
| T108 | 4, 12, 21, 32, 55, 89, 109, 140, 174, 232 |
| T109 | 4, 11, 23, 35, 54, 80, 113, 146, 176, 215 |
| T110 | 4, 11, 23, 35, 54, 80, 113, 146, 176, 215 |
| T111 | 4, 11, 24, 37, 51, 81, 116, 148, 172, 213 |
| T112 | 4, 11, 21, 36, 54, 80, 110, 144, 180, 217 |
| T113 | 4, 11, 20, 30, 47, 76, 113, 147, 178, 212 |
| T114 | 4, 11, 20, 30, 47, 76, 113, 147, 178, 212 |

TABLE 6-continued

Polymorph C in P1 Space Group

| T atom | Coordination Sequence |
|---|---|
| T115 | 4, 11, 20, 30, 47, 76, 113, 147, 172, 211 |
| T116 | 4, 11, 20, 30, 47, 76, 113, 145, 175, 215 |
| T117 | 4, 11, 20, 30, 47, 76, 113, 149, 175, 208 |
| T118 | 4, 11, 20, 30, 47, 76, 113, 149, 175, 208 |
| T119 | 4, 11, 20, 30, 47, 76, 113, 145, 175, 215 |
| T120 | 4, 11, 20, 30, 47, 76, 113, 147, 172, 211 |
| T121 | 4, 12, 19, 35, 51, 87, 124, 140, 166, 214 |
| T122 | 4, 12, 19, 35, 51, 87, 124, 140, 166, 214 |

TABLE 7

Polymorph D in P2 Space Group

| T atom | Coordination Sequence |
|---|---|
| T1 | 4, 11, 20, 30, 46, 77, 115, 147, 168, 213 |
| T2 | 4, 12, 24, 33, 53, 85, 119, 141, 175, 223 |
| T3 | 4, 10, 21, 36, 56, 80, 105, 143, 191, 229 |
| T4 | 4, 11, 22, 37, 56, 81, 112, 149, 186, 226 |
| T5 | 4, 12, 18, 33, 52, 80, 112, 140, 177, 228 |
| T6 | 4, 12, 18, 35, 59, 83, 110, 137, 189, 229 |
| T7 | 4, 10, 21, 36, 56, 80, 107, 144, 190, 233 |
| T8 | 4, 9, 18, 33, 55, 81, 108, 143, 184, 219 |
| T9 | 4, 9, 18, 33, 55, 81, 108, 143, 184, 219 |
| T10 | 4, 12, 21, 36, 53, 77, 111, 148, 176, 218 |
| T11 | 4, 11, 23, 35, 54, 80, 113, 146, 176, 216 |
| T12 | 4, 11, 20, 29, 47, 82, 117, 141, 165, 215 |
| T13 | 4, 10, 21, 36, 56, 80, 107, 144, 193, 230 |
| T14 | 4, 11, 22, 37, 56, 81, 108, 144, 189, 227 |
| T15 | 4, 12, 18, 33, 52, 80, 110, 141, 175, 225 |
| T16 | 4, 12, 18, 34, 58, 82, 109, 136, 185, 229 |
| T17 | 4, 10, 21, 36, 56, 78, 108, 144, 188, 228 |
| T18 | 4, 9, 18, 33, 55, 81, 108, 142, 181, 222 |
| T19 | 4, 12, 20, 34, 54, 79, 110, 144, 177, 219 |
| T20 | 4, 9, 18, 33, 55, 81, 108, 142, 183, 222 |
| T21 | 4, 12, 21, 36, 54, 81, 115, 146, 174, 222 |
| T22 | 4, 11, 20, 35, 58, 80, 106, 146, 192, 231 |
| T23 | 4, 12, 18, 33, 52, 80, 112, 138, 173, 229 |
| T24 | 4, 11, 20, 35, 58, 78, 105, 147, 192, 224 |
| T25 | 4, 12, 18, 33, 52, 80, 109, 140, 177, 223 |
| T26 | 4, 12, 21, 32, 55, 89, 107, 139, 175, 233 |
| T27 | 4, 12, 20, 33, 53, 79, 112, 141, 175, 210 |
| T28 | 4, 12, 24, 33, 52, 82, 119, 145, 173, 219 |
| T29 | 4, 11, 23, 35, 55, 83, 115, 145, 176, 222 |
| T30 | 4, 12, 19, 36, 58, 79, 111, 141, 188, 226 |
| T31 | 4, 12, 22, 33, 54, 81, 118, 147, 169, 218 |
| T32 | 4, 11, 20, 35, 58, 80, 104, 143, 191, 232 |
| T33 | 4, 12, 18, 33, 52, 80, 112, 143, 175, 226 |
| T34 | 4, 11, 20, 35, 58, 78, 105, 146, 187, 227 |
| T35 | 4, 12, 18, 33, 52, 80, 112, 140, 178, 229 |
| T36 | 4, 12, 21, 32, 55, 89, 109, 140, 174, 233 |
| T37 | 4, 12, 20, 33, 54, 82, 116, 142, 174, 216 |
| T38 | 4, 11, 20, 29, 47, 82, 117, 141, 165, 218 |
| T39 | 4, 10, 21, 36, 56, 80, 105, 145, 196, 226 |
| T40 | 4, 11, 22, 37, 56, 79, 108, 147, 185, 227 |
| T41 | 4, 12, 18, 33, 52, 80, 110, 138, 177, 227 |
| T42 | 4, 12, 19, 35, 57, 79, 112, 139, 181, 227 |
| T43 | 4, 10, 21, 36, 56, 78, 106, 145, 190, 226 |
| T44 | 4, 9, 18, 33, 55, 81, 108, 142, 181, 220 |
| T45 | 4, 9, 18, 33, 55, 81, 108, 142, 183, 220 |
| T46 | 4, 12, 20, 34, 55, 82, 112, 143, 178, 222 |
| T47 | 4, 11, 21, 36, 54, 80, 110, 144, 180, 218 |
| T48 | 4, 11, 20, 30, 46, 77, 115, 147, 171, 207 |
| T49 | 4, 10, 21, 36, 56, 78, 106, 145, 191, 224 |
| T50 | 4, 12, 18, 33, 52, 80, 109, 142, 181, 225 |
| T51 | 4, 12, 18, 33, 52, 80, 109, 142, 181, 225 |
| T52 | 4, 10, 21, 36, 56, 78, 108, 146, 191, 226 |
| T53 | 4, 9, 18, 33, 55, 81, 108, 143, 182, 221 |
| T54 | 4, 12, 22, 33, 55, 82, 116, 146, 172, 219 |
| T55 | 4, 9, 18, 33, 55, 81, 108, 143, 182, 221 |
| T56 | 4, 11, 24, 37, 52, 84, 118, 147, 172, 220 |
| T57 | 4, 11, 20, 30, 47, 76, 113, 144, 175, 218 |
| T58 | 4, 11, 20, 30, 47, 76, 113, 144, 171, 214 |

TABLE 7-continued

Polymorph D in P2 Space Group

| T atom | Coordination Sequence |
|---|---|
| T59 | 4, 11, 20, 30, 47, 76, 113, 145, 175, 213 |
| T60 | 4, 11, 20, 30, 47, 76, 113, 149, 175, 210 |
| T61 | 4, 12, 19, 35, 50, 84, 120, 139, 167, 209 |

TABLE 8

Polymorph E in P-1 Space Group

| T atom | Coordination Sequence |
|---|---|
| T1 | 4, 11, 20, 30, 46, 77, 115, 147, 168, 213 |
| T2 | 4, 12, 24, 33, 53, 85, 119, 141, 175, 223 |
| T3 | 4, 10, 21, 36, 56, 80, 105, 143, 191, 231 |
| T4 | 4, 11, 22, 37, 56, 81, 112, 149, 186, 226 |
| T5 | 4, 12, 18, 33, 52, 80, 112, 140, 175, 227 |
| T6 | 4, 12, 18, 35, 59, 83, 110, 137, 189, 229 |
| T7 | 4, 10, 21, 36, 56, 80, 107, 144, 190, 231 |
| T8 | 4, 9, 18, 33, 55, 81, 108, 143, 184, 219 |
| T9 | 4, 9, 18, 33, 55, 81, 108, 143, 184, 219 |
| T10 | 4, 12, 21, 36, 53, 77, 111, 148, 176, 218 |
| T11 | 4, 11, 23, 35, 54, 80, 113, 146, 176, 216 |
| T12 | 4, 11, 20, 29, 47, 82, 117, 141, 165, 215 |
| T13 | 4, 10, 21, 36, 56, 78, 108, 144, 190, 228 |
| T14 | 4, 11, 20, 35, 58, 80, 104, 143, 191, 230 |
| T15 | 4, 12, 18, 33, 52, 80, 112, 141, 173, 228 |
| T16 | 4, 12, 18, 34, 58, 82, 109, 136, 185, 229 |
| T17 | 4, 10, 21, 36, 56, 80, 107, 144, 191, 230 |
| T18 | 4, 9, 18, 33, 55, 81, 108, 142, 183, 220 |
| T19 | 4, 9, 18, 33, 55, 81, 108, 142, 181, 224 |
| T20 | 4, 11, 20, 35, 58, 80, 106, 146, 192, 231 |
| T21 | 4, 12, 18, 33, 52, 80, 112, 138, 175, 230 |
| T22 | 4, 11, 20, 35, 58, 78, 105, 147, 192, 224 |
| T23 | 4, 12, 18, 33, 52, 80, 109, 140, 179, 225 |
| T24 | 4, 12, 21, 32, 55, 89, 107, 139, 175, 233 |
| T25 | 4, 12, 20, 33, 53, 79, 112, 141, 175, 210 |
| T26 | 4, 12, 24, 33, 52, 82, 119, 145, 173, 219 |
| T27 | 4, 11, 23, 35, 55, 83, 115, 145, 176, 222 |
| T28 | 4, 11, 20, 35, 58, 78, 105, 146, 187, 225 |
| T29 | 4, 12, 18, 33, 52, 80, 112, 138, 176, 230 |
| T30 | 4, 12, 21, 32, 55, 89, 109, 140, 174, 233 |
| T31 | 4, 12, 20, 33, 54, 82, 116, 142, 174, 216 |
| T32 | 4, 11, 20, 29, 47, 82, 117, 141, 165, 218 |
| T33 | 4, 10, 21, 36, 58, 78, 106, 145, 192, 226 |
| T34 | 4, 12, 19, 35, 57, 79, 112, 139, 181, 227 |
| T35 | 4, 10, 21, 36, 56, 80, 105, 145, 194, 226 |
| T36 | 4, 9, 18, 33, 55, 81, 108, 142, 183, 218 |
| T37 | 4, 9, 18, 33, 55, 81, 108, 142, 181, 222 |
| T38 | 4, 12, 22, 33, 55, 82, 116, 146, 172, 219 |
| T39 | 4, 11, 20, 30, 46, 77, 115, 147, 171, 207 |
| T40 | 4, 10, 21, 36, 56, 78, 106, 145, 191, 226 |
| T41 | 4, 11, 22, 37, 56, 79, 110, 150, 186, 226 |
| T42 | 4, 12, 18, 33, 52, 80, 109, 142, 179, 223 |
| T43 | 4, 10, 21, 36, 56, 78, 108, 146, 191, 224 |
| T44 | 4, 9, 18, 33, 55, 81, 108, 143, 182, 221 |
| T45 | 4, 9, 18, 33, 55, 81, 108, 143, 182, 221 |
| T46 | 4, 11, 20, 30, 47, 76, 113, 144, 173, 216 |
| T47 | 4, 11, 20, 30, 47, 76, 113, 144, 173, 216 |
| T48 | 4, 11, 20, 30, 47, 76, 113, 147, 175, 212 |
| T49 | 4, 11, 20, 30, 47, 76, 113, 147, 175, 211 |
| T50 | 4, 12, 19, 35, 50, 84, 120, 139, 167, 209 |
| T51 | 4, 12, 21, 36, 54, 81, 115, 146, 174, 222 |
| T52 | 4, 12, 19, 36, 58, 79, 111, 141, 188, 226 |
| T53 | 4, 12, 20, 34, 54, 79, 110, 144, 177, 219 |
| T54 | 4, 11, 21, 36, 54, 80, 110, 144, 180, 218 |
| T55 | 4, 11, 22, 37, 56, 81, 108, 144, 189, 229 |
| T56 | 4, 12, 18, 33, 52, 80, 110, 143, 177, 223 |
| T57 | 4, 12, 22, 33, 54, 81, 118, 147, 169, 218 |
| T58 | 4, 11, 24, 37, 52, 84, 118, 147, 172, 220 |
| T59 | 4, 11, 22, 37, 56, 79, 108, 147, 185, 229 |
| T60 | 4, 12, 18, 33, 52, 80, 110, 140, 179, 226 |
| T61 | 4, 12, 20, 34, 55, 82, 112, 143, 178, 222 |

TABLE 9

Polymorph F in P-1 Space Group

| T atom | Coordination Sequence |
|---|---|
| T1 | 4, 11, 20, 30, 46, 77, 115, 147, 168, 215 |
| T2 | 4, 12, 24, 33, 52, 82, 117, 142, 174, 220 |
| T3 | 4, 10, 21, 36, 56, 80, 105, 145, 193, 227 |
| T4 | 4, 11, 22, 37, 56, 81, 110, 147, 190, 226 |
| T5 | 4, 12, 18, 33, 52, 80, 112, 140, 175, 227 |
| T6 | 4, 12, 18, 35, 59, 83, 110, 137, 189, 229 |
| T7 | 4, 10, 21, 36, 56, 80, 107, 144, 190, 231 |
| T8 | 4, 9, 18, 33, 55, 81, 108, 143, 184, 219 |
| T9 | 4, 9, 18, 33, 55, 81, 108, 143, 184, 217 |
| T10 | 4, 12, 21, 36, 53, 78, 113, 147, 173, 219 |
| T11 | 4, 11, 23, 35, 55, 83, 115, 145, 176, 223 |
| T12 | 4, 11, 20, 30, 46, 77, 115, 147, 171, 206 |
| T13 | 4, 10, 21, 36, 56, 78, 106, 145, 191, 226 |
| T14 | 4, 11, 20, 35, 58, 80, 106, 146, 192, 227 |
| T15 | 4, 12, 18, 33, 52, 80, 109, 142, 177, 221 |
| T16 | 4, 12, 18, 35, 59, 83, 110, 137, 189, 229 |
| T17 | 4, 10, 21, 36, 56, 78, 108, 144, 189, 228 |
| T18 | 4, 9, 18, 33, 55, 81, 108, 143, 182, 223 |
| T19 | 4, 9, 18, 33, 55, 81, 108, 143, 182, 221 |
| T20 | 4, 11, 20, 35, 58, 80, 106, 146, 192, 227 |
| T21 | 4, 12, 18, 33, 52, 80, 112, 138, 177, 232 |
| T22 | 4, 11, 20, 35, 58, 78, 107, 149, 188, 222 |
| T23 | 4, 12, 18, 33, 52, 80, 109, 140, 179, 225 |
| T24 | 4, 12, 21, 32, 55, 89, 107, 139, 175, 234 |
| T25 | 4, 12, 20, 33, 53, 79, 112, 141, 175, 211 |
| T26 | 4, 12, 24, 33, 52, 82, 117, 142, 174, 220 |
| T27 | 4, 11, 23, 35, 55, 83, 115, 145, 176, 223 |
| T28 | 4, 11, 20, 35, 58, 78, 107, 149, 188, 222 |
| T29 | 4, 12, 18, 33, 52, 80, 112, 140, 175, 227 |
| T30 | 4, 12, 21, 32, 55, 89, 107, 139, 175, 234 |
| T31 | 4, 12, 20, 33, 53, 79, 112, 141, 175, 211 |
| T32 | 4, 11, 20, 30, 46, 77, 115, 147, 168, 215 |
| T33 | 4, 10, 21, 36, 56, 80, 105, 145, 193, 227 |
| T34 | 4, 12, 19, 36, 58, 80, 113, 140, 185, 227 |
| T35 | 4, 10, 21, 36, 56, 80, 107, 144, 190, 231 |
| T36 | 4, 9, 18, 33, 55, 81, 108, 143, 184, 219 |
| T37 | 4, 9, 18, 33, 55, 81, 108, 143, 184, 217 |
| T38 | 4, 12, 22, 33, 54, 79, 114, 147, 171, 216 |
| T39 | 4, 11, 20, 30, 46, 77, 115, 147, 171, 206 |
| T40 | 4, 10, 21, 36, 56, 78, 106, 145, 191, 226 |
| T41 | 4, 11, 22, 37, 56, 79, 110, 150, 186, 226 |
| T42 | 4, 12, 18, 33, 52, 80, 109, 142, 177, 221 |
| T43 | 4, 10, 21, 36, 56, 78, 108, 144, 189, 228 |
| T44 | 4, 9, 18, 33, 55, 81, 108, 143, 182, 223 |
| T45 | 4, 9, 18, 33, 55, 81, 108, 143, 182, 221 |
| T46 | 4, 11, 20, 30, 47, 76, 113, 144, 173, 216 |
| T47 | 4, 11, 20, 30, 47, 76, 113, 144, 173, 216 |
| T48 | 4, 11, 20, 30, 47, 76, 113, 144, 173, 216 |
| T49 | 4, 11, 20, 30, 47, 76, 113, 144, 173, 216 |
| T50 | 4, 12, 19, 35, 49, 81, 116, 138, 168, 204 |
| T51 | 4, 12, 21, 36, 53, 78, 113, 147, 173, 219 |
| T52 | 4, 12, 19, 36, 58, 80, 113, 140, 185, 227 |
| T53 | 4, 12, 20, 34, 54, 79, 110, 144, 177, 219 |
| T54 | 4, 11, 21, 36, 54, 80, 110, 144, 180, 219 |
| T55 | 4, 11, 22, 37, 56, 81, 110, 147, 190, 226 |
| T56 | 4, 12, 18, 33, 52, 80, 109, 140, 179, 225 |
| T57 | 4, 12, 22, 33, 54, 79, 114, 147, 171, 216 |
| T58 | 4, 11, 24, 37, 53, 87, 120, 146, 172, 227 |
| T59 | 4, 11, 22, 37, 56, 79, 110, 150, 186, 226 |
| T60 | 4, 12, 18, 33, 52, 80, 112, 138, 177, 232 |
| T61 | 4, 12, 20, 34, 54, 79, 110, 144, 177, 219 |

TABLE 10

Polymorph G in P4$_2$/mmc Space Group

| T atom | Coordination Sequence |
|---|---|
| T1 | 4, 10, 19, 33, 52, 76, 106, 136, 170, 213 |
| T2 | 4, 10, 21, 36, 54, 74, 103, 142, 189, 222 |
| T3 | 4, 11, 20, 35, 52, 73, 101, 141, 180, 221 |
| T4 | 4, 12, 18, 33, 52, 78, 106, 138, 174, 220 |
| T5 | 4, 9, 18, 33, 55, 81, 108, 140, 174, 209 |
| T6 | 4, 11, 20, 29, 47, 80, 110, 132, 162, 212 |
| T7 | 4, 12, 20, 31, 49, 77, 109, 128, 175, 213 |
| T8 | 4, 10, 20, 32, 49, 77, 112, 141, 162, 204 |
| T9 | 4, 9, 18, 33, 54, 79, 105, 136, 174, 212 |
| T10 | 4, 11, 20, 30, 47, 76, 109, 137, 172, 218 |
| T11 | 4, 12, 20, 24, 48, 88, 104, 124, 148, 250 |

As-Made EMM-41 Material

The as-made (e.g., without treatment to remove the SDA) EMM-41 material may have at least four (4), or preferably all of the XRD peaks in degree 2-theta selected from Table 2A:

TABLE 2A

| degrees 2-theta (±0.2) | d-spacing (Å) | relative integrated intensity [100 × I/(Io)] |
|---|---|---|
| 7.25* | 12.19 | 15-30 |
| 7.42* | 11.90 | 70-100 |
| 9.06 | 9.76 | 30-50 |
| 19.39 | 4.57 | 10-25 |
| 22.79 | 3.90 | 70-100 |

*Peaks form a composite feature.

The as-made (e.g., without treatment to remove the SDA) EMM-41 material may have at least six (6), or seven (7), or eight (8), or preferably all of the XRD peaks with the degree 2-theta and d-spacing values selected from Table 2B, wherein the d-spacing values have a deviation determined based on the corresponding deviation ±0.20 degree 2-theta when converted to the corresponding values for d-spacing using Bragg's law:

TABLE 2B

| degrees 2-theta (±0.2) | d-spacing (Å) | relative integrated intensity [100 × I/(Io)] |
|---|---|---|
| 7.25* | 12.19 | 15-30 |
| 7.42* | 11.90 | 70-100 |
| 8.04 | 10.98 | 10-20 |
| 9.06 | 9.76 | 30-50 |
| 10.32 | 8.57 | 10-20 |
| 19.39 | 4.57 | 10-25 |
| 22.27 | 3.99 | 20-30 |
| 22.79 | 3.90 | 70-100 |
| 26.23 | 3.39 | 20-35 |

*Peaks form a composite feature.

In one or more aspects, the as-made EMM-41 material may optionally be represented by the molecular formula of Formula B:

$$(n)Q:(v)X_2O_3:YO_2 \quad \text{Formula B,}$$

wherein $0.01 \leq n \leq 0.1$, $0.000 \leq v \leq 0.05$ or $0.0005 \leq v \leq 0.05$, Q is an organic structure directing agent (SDA), X is a trivalent element, and Y is a tetravalent element. O is oxygen. X may be selected from B, Al, Fe, and Ga, or a mixture thereof. For example, X may comprise or be Al or B. Y may be selected from Si, Ge, Sn, Ti and Zr, or a mixture thereof. For example, Y may comprise or be Si. Formula B can represent the framework of a typical as-made EMM-41 material with SDA, and is not meant to be the sole representation of such material. The as-made EMM-41 material may contain impurities that are not represented by Formula B. Further, Formula B does not include the protons and charge compensating ions that may be present in the as-made EMM-41 material.

The variable v represents the molar relationship of $X_2O_3$ in Formula B. The values for variable v in Formula A are the same as those described herein for Formula B. The variable n represents the molar relationship of SDA (Q) in Formula B. For example, when n is 0.1, the molar ratio of Q to Y is 0.1. When n is 0.3, the molar ratio of Q to Y is 0.3. The molar ratio of Q to Y may be 0.01 to 0.5, or 0.01 to 0.2, or 0.15 to 0.3, or 0.15 to 0.50, or about 0.25.

Method of Making EMM-41 Materials

The method for preparing the as-made EMM-41 materials may comprise the following steps:

(a) preparing a reaction mixture comprising the following components:
  (i) a source of an oxide of a tetravalent element (Y), preferably TMOS;
  (ii) optionally, a source of a trivalent element (X), preferably aluminum;
  (iii) a source of hydroxide ions (OH), preferably a hydroxide of the SDA (Q);
  (iv) a source of fluoride ions (F), preferably hydrogen fluoride;
  (v) an organic structure directing agent (Q) which comprises a bispyrrolidinium dication;
  (vi) water; and
  (vii) optionally, a source of zeolite seeds in the amount of 0 to 10 wt. % based on the weight of the tetravalent element (X), wherein the reaction mixture has a composition in terms of molar ratios within the following ranges:
    $YO_2/X_2O_3$=10 to infinity, preferably 20 to infinity, more preferably 40 to infinity;
    $H_2O/YO_2$=2 to 15, preferably 2 to 10, more preferably 2 to 8;
    $OH^-/YO_2$=0.25 to 2 or 0.25 to 1, preferably 0.8 to 1.2 or 0.35 to 0.75;
    $F/YO_2$=0.35 to 1, preferably 0.4 to 0.6;
    $Q/YO_2$=0.01 to 0.50 or 0.10 to 0.5, preferably 0.15 to 0.3;

(b) mixing and/or heating said reaction mixture of step (a) under crystallization conditions including a temperature of from about 90° C. to about 190° C., preferably 90° C. to 175° C., to form crystals of a resulting mixture; and (c) recovering at least a portion of said crystals from said resulting mixture of step (b), preferably, as said as-made EMM-41 material having an XRD peaks of the pattern shown in Table 2A, preferably as shown in Table 2B.

The as-made EMM-41 material may be prepared by a process that includes isolating seed crystals of EMM-41 materials from a composition. Alternatively, the seeds may be heterostructural seeds, such as for examples, seeds from ITQ-24 or ITQ-33. The as-made EMM-41 may be made without seeds. The content of the zeolite seeds in the reaction mixture is from 0 to 10 wt. % or from 0 to 7 wt. %, or from 0 to 5 wt. % of from 0 to 1 wt. %, based on the weight of the tetravalent element (X).

The structure directing agent, SDA, designated as (Q), may also comprise a source of hydroxide ions, such as for example, a bispyrrolidium dication, where hydroxide is one or both of the counter ions.

In one or more embodiments, the reaction mixture includes at least the SDA (Q) as a hydroxide, e.g., a bispyrrolidinium hydroxide, and a source of an oxide of a tetravalent element (Y), a source of fluoride ions and water. Optionally, the reaction mixture may include a source of trivalent element (X).

In other embodiment, the reaction mixture is prepared where a solution of a source of the SDA (Q) in hydroxide form, such as bispyrrolidinium hydroxide, is first combined with a solution of a source of the tetravalent element (Y), such as tetramethylorthosilicate (TMOS), and freeze-dried to remove water. The freeze-dried product in then re-slurried with water to the target $H_2O/SiO_2$ molar ratio target. Then, the source of fluoride ion is added to the re-slurried product to form the final reaction mixture. This reaction mixture is then mixed and/or heated under crystallization conditions including a temperature of from about 90° C. to about 175° C. or from about 90° C. to about 120° C., to form crystals which are recovered.

The source of the oxide of a tetravalent element Y may also include a source of a trivalent element X, such as for example, a precipitate aluminosilicate.

The reaction mixture may have a molar ratio of $YO_2$ to $H_3XO_3$ (e.g., $H_3BO_3$) or $YO_2$ to $X_2O_3$ (e.g., $Al_2O_3$) of 10 to infinity (e.g., 10 to 30). The reaction mixture may also have a molar ratio of $H_2O$ to $YO_2$ of 1 to 50 (e.g., 3 to 10). The reaction mixture may also have a molar ratio of $OH^-$ to $YO_2$ of 0.25 to 1 (e.g., 0.35 to 0.75). The reaction mixture may have a molar ratio of Q to $YO_2$ of 0.01 to 0.5 (e.g., 0.01 to 0.5, or 0.15 to 0.3, or 0.05 to 0.2). The reaction mixture may have a molar ratio of F to $YO_2$ of 0.35 to 1 (e.g., 0.4 to 0.6).

The trivalent element X used in the reaction mixtures may be boron, B, resulting in the as-made material being a borosilicate. The trivalent element used in the reaction mixture may be aluminum, Al, resulting in the as-made material being an aluminosilicate.

Ammonium exchange actually introduces extraframework ammonium cations. Optionally, the as-made EMM-41 material may be prepared from a reaction mixture which contains a trivalent element X source with a hydroxide solution of SDA, and then subsequently adding a tetravalent Y source to the reaction mixture.

In one or more aspects, the mixture is mixed by a mechanical process such as stirring or high shear blending to assure suitable homogenization of the reaction mixture, for example, using dual asymmetric centrifugal mixing (e.g., a FlackTek speed mixer) with a mixing speed of 1000 to 3000 rpm (e.g., 2000 rpm). The mixing may be employed after solvent, such as water, adjustment (e.g., where the desired water to silica ratio is achieved).

Depending on the nature of the reagents in the base mixture, the amount of solvent (e.g., water from the hydroxide solution, and optionally methanol and ethanol from the hydrolysis of silica sources) of the reaction mixture may be removed such that a desired solvent to $YO_2$ molar ratio is achieved for the resulting mixture. Suitable methods for reducing the solvent content may include evaporation under a static or flowing atmosphere such as ambient air, dry nitrogen, dry air, or by spray drying or freeze drying. Water may be added to the resulting mixture to achieve a desired $H_2O/YO_2$ molar ratio when too much water is removed during the solvent removal process.

The process may further include mixing the reaction mixture. The mixed mixture is then subject to crystallization conditions suitable for the EMM-41 material to form.

The process may further include heating the composition, either before or after mixing.

Crystallization of an EMM-41 material may be carried out under static or stirred conditions in a suitable reactor vessel, such as for example, polypropylene jars or TEFLON® lined or stainless steel (SS) autoclaves placed in a convection oven maintained at a temperature of about 100 to about 200° C. for a period of time sufficient for crystallization to occur, e.g., from about 1 day to about 30 days (e.g., 1 day to 12, or 14 or 16 days, or 1 day to 7 days). Unless indicated otherwise herein, the temperature measured is the temperature of the surrounding environment of the material being heated, for example the temperature of the atmosphere in which the material is heated. Thereafter, the solid crystals of the as-made EMM-41 material are separated from the liquid (e.g., by filtration or centrifugation) and recovered.

Examples of sources of the tetravalent element Y may be selected from colloidal suspensions of silica, precipitated silica, fumed silica, alkali metal silicates, tetraalkyl orthosilicates, such as, for example, tetraethyl orthosilicate or tetramethyl orthosilicate, and germanium oxide, or a mixture thereof. Preferably, the source of the tetravalent element is tetramethyl orthosilicate (TMOS). Other examples of sources of silica may include LUDOX® (e.g., LUDOX® LS-30, LUDOX® AS-40) colloidal silica, SIPERNAT® or ULTRASIL® precipitated silica, CARBOSPERSE™ fumed silica suspension, or a mixture thereof.

In one or more aspects, the trivalent element X may be boron or aluminum. Suitable sources of aluminum may be selected from hydrated alumina, aluminum hydroxide, alkali metal aluminates, aluminum alkoxides, and water-soluble aluminum salts, such as aluminum nitrate, or a mixture thereof. Suitable sources of boron may be selected from boric acid, sodium tetraborate, and potassium tetraborate, or a mixture thereof. For example, the boron source may be boric acid.

In one or more aspects, the EMM-41 material may be prepared using boric acid as the source of the trivalent element. The as-made EMM-41 comprising boron may be thermally-treated (e.g., at least partially calcined) to remove part or all of the SDA.

Optionally, the material (wherein part or all of the SDA has been removed) having X is B and Y is Si may be contacted with an Al source under conditions sufficient to exchange the B in the framework with Al. For example, the thermally-treated EMM-41 comprising boron may be converted to an aluminosilicate by heating the thermally-treated EMM-41 material comprising boron with a solution of $Al_2(SO_4)_3$ (e.g., in a sealed autoclave in a convection oven for overnight maintained at 100° C. or at boiling temperature in an open system). The aluminum treated EMM-41 may then be recovered by filtration and washed with deionized water.

Part or all of the SDA used during the synthesis of an as-made EMM-41 material may be removed by thermal treatment, ozone treatment, or other treatments to form the EMM-41 material that is substantially free of the SDA (e.g., greater than 50%, 60%, 70%, 80%, 90%, 95% or 99% (based on weight) free of SDA).

Removal of SDA may be carried out using thermal treatment (e.g., calcination) in which the as-made EMM-41 material is heated in an atmosphere selected from air, nitrogen, or a mixture thereof at a temperature sufficient to remove part or all of the SDA. While subatmospheric pressure may be employed for the thermal treatment, atmospheric pressure is desired for reasons of convenience. The thermal treatment may be performed at a temperature up to 700° C., e.g., from 400° C. to 700° C. The thermal treatment (e.g., calcination) may be carried out in a box furnace in dry air, which has been exposed to a drying tube containing drying agents that remove water from the air. The heating may be carried out for a few hours to 14 days at 400° C. to 700° C. (e.g., 540° C.). The heating may first be carried out under a nitrogen atmosphere up to 400° C. and then the atmosphere may be switched to air at 400° C. to 600° C.

The as-made EMM-41 material includes a structure directing agent (SDA), e.g., a bispyrrolidinium dication. Alternative methods of synthesizing the EMM-41 material may be carried out without the use of an SDA. Suitable sources of the structure directing agents may be selected from the hydroxides and/or salts of the relevant diquaternary ammonium compounds.

In one or more aspects, a structure directing agent (SDA) useful for synthesizing a zeolite, for example an as-made EMM-41 material, may be Compound I having the following structure:

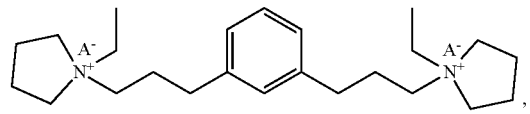

wherein A is an ion.

Where each of A is a hydroxide, the SDA above is 1,1'-(3,3'-(1,3-phenylene)bis(propane-3,1-diyl))bis(1-ethylpyrrolidinium).

In one or more embodiments, one or both of A are the same or different in Compound I. For example, A may be tosylate, hydroxide (OH), or halide, such as I or Br. For example, both A ions may be OH.

In one or more embodiments, the as-made EMM-41 material has within its pore structure a bispyrrolidinium dication which comprises the following structure of Compound I, above. The method for preparing Compound I is described in the Synthesis of Organic Structure Directing Agent (Compound I), below.

Uses of EMM-41 Material

EMM-41 materials (wherein part or all of the SDA is removed) may be used as an adsorbent or in an aluminosilicate form, as a catalyst to catalyze a wide variety of organic compound conversion processes. Examples of chemical conversion processes, which are effectively catalyzed by the modified EMM-41 materials described herein, either alone or in combination with one or more other catalytically active substances (including other crystalline catalysts), include those requiring a catalyst with acid activity. Examples of organic conversion processes, which may be catalyzed by the modified EMM-41 materials described herein include cracking, hydrocracking, disproportionation, alkylation, oligomerization, and isomerization.

EMM-41 materials (wherein part or all of the SDA is removed), when employed either as an adsorbent or as a catalyst, may be dehydrated, at least partially. Such dehydration may be accomplished by heating the material in a surrounding atmosphere at a temperature in the range of 200 to 370° C., the atmosphere may be selected from air, nitrogen, or a mixture thereof, and at atmospheric, subatmospheric or superatmospheric pressures for between 30 minutes and 48 hours. Dehydration may also be performed at room temperature by placing the EMM-41 materials in a vacuum; however, a longer period of time is required to obtain a sufficient amount of dehydration.

In one or more embodiments, the EMM-41 material may be used in a process for selectively separating one or more desired components of a feedstock from remaining components of the feedstock. In the process, the feedstock is contacted with a sorbent at effective sorption conditions, thereby forming a sorbed product and an effluent product. The sorbent comprises an active form of any one of the synthetic porous crystalline materials of this invention. One or more of the desired components are recovered from either the sorbed product or the effluent product.

EMM-41 materials (wherein part or all of the SDA is removed) may be combined with a hydrogenating component. The hydrogenating component may be selected from molybdenum, tungsten, rhenium, nickel, cobalt, chromium, manganese, or a noble metal, such as platinum or palladium where a hydrogenation-dehydrogenation function is to be performed. Such hydrogenating components may be incorporated into the composition by way of one or more of the following processes: co-crystallizing; exchanging into the composition to the extent a Group IIIA element, e.g., aluminum, is in the structure; impregnating therein or physically admixing therewith. For example, such hydrogenating components may be impregnated into the EMM-41 material. In the case of platinum, the EMM-41 materials may be impregnated with a solution containing a platinum metal-containing ion. Suitable platinum compounds for impregnating may be selected from chloroplatinic acid, platinous chloride, compounds containing a platinum amine complex, or a mixture thereof.

EMM-41 materials (wherein part or all of the SDA is removed) may be incorporated with another material resistant to the temperatures and other conditions employed in organic conversion processes. Such resistant materials may be selected from active materials, inactive materials, synthetic zeolites, naturally occurring zeolites, inorganic materials or a mixture thereof. Examples of such resistant materials may be selected from clays, silica, metal oxides such as alumina, or a mixture thereof. The inorganic material may be either naturally occurring, or in the form of gelatinous precipitates or gels, including mixtures of silica and metal oxides. Use of a resistant material in conjunction with an EMM-41 material, i.e., combined therewith or present during synthesis of the as-made EMM-41 crystal, which crystal is active, tends to change the conversion and/or selectivity of the catalyst in certain organic conversion processes. Inactive resistant materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said inactive resistant materials, i.e., clays, oxides, etc., function as binders for the catalyst. A catalyst having good crush strength can be beneficial because in commercial use, it is desirable to prevent the catalyst from breaking down into powder-like materials.

Naturally occurring clays which may be composited with EMM-41 materials include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays may be used in the raw state as originally mined or initially subjected to calcination, acid treatment or chemical modification. Binders useful for compositing with EMM-41 materials also include inorganic oxides selected from silica, zirconia, titania, magnesia, beryllia, alumina, or a mixture thereof.

EMM-41 materials (wherein part or all of the SDA is removed) may be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia.

The relative proportions of EMM-41 material and inorganic oxide matrix may vary widely, with the EMM-41 material content ranging from about 1 to about 90 percent by weight, of the composite or, when the composite is prepared in the form of beads, in the range of about 2 to about 80 weight percent of the composite.

As used herein, and unless otherwise specified, a numeric value or range of values may deviate to an extent deemed reasonable to one of ordinary skill in the relevant art. It is well known that instrument variation and other factors can affect the numerical values. Such deviation, unless otherwise specified, may be plus or minus 2%, 5%, 10%, 15%, 20%, 25%, or 30% of the numeric value or range of values indicated.

The EMM-41 materials described herein may be at least 50%, at least 60%, at least 70%, at least 80%, at least 90%, at least 95%, at least 97%, or at least 99% (e.g., 99.5% or 99.9%) by weight pure EMM-41 material, based on the total weight of the composition, by quantification using XRD or NMR spectroscopy (e.g., by measuring the area or the relative intensity of the relevant peaks (which may be normalized to account for the composite peaks in the two-theta range of 7.2-7.4 degrees), or by other known methods appropriate for such determination. The remainder of the material is non-EMM-41 material, which may be structure directing agent, amorphous material, other impurities, or a mixture thereof.

The EMM-41 material described herein is substantially crystalline. As used herein, the term "crystalline" refers to a crystalline solid form of a material, including, but not limited to, a single-component or multiple-component crystal form, e.g., including solvates, hydrates, and a co-crystal. Crystalline can mean having a regularly repeating and/or ordered arrangement of atoms, and possessing a distinguishable crystal lattice. For example, crystalline EMM-41 can have different water or solvent content. The different crystalline lattices can be identified by solid state characterization methods such as by XRD (e.g., powder XRD). Other characterization methods known to a person of ordinary skill in the relevant art can further help identify the crystalline form as well as help determine stability and solvent/water content.

As used herein, the term "substantially crystalline" means a majority (greater than 50%) of the weight of a sample of a solid material described is crystalline and the remainder of the sample is a non-crystalline form. In one or more aspects, a substantially crystalline sample has at least 95% crystallinity (e.g., 5% of the non-crystalline form), at least 96% crystallinity (e.g., 4% of the non-crystalline form), at least 97% crystallinity (e.g., 3% of the non-crystalline form), at least 98% crystallinity (e.g., about 2% of the non-crystalline form), at least 99% crystallinity (e.g., 1% of the non-crystalline form), and 100% crystallinity (e.g., 0% of the non-crystalline form).

The micropore volume of the modified EMM-41 materials described herein can be determined using methods known in the relevant art. For example, the materials can be measured with nitrogen physisorption, and the data can be analyzed by the t-plot method described in Lippens, B. C. et al., "Studies on pore system in catalysts: V. The t method", *J. Catal.*, 4, 319 (1965), which describes micropore volume method and is incorporated herein by reference.

As used herein, the term "alkyl" refers to a saturated hydrocarbon group that may be straight-chained or branched. An alkyl group corresponds to an alkane with one C—H bond replaced by the point of attachment of the alkyl group to the remainder of the compound. The alkyl group may contain from 1 to 6 carbon atoms, from 1 to 4 carbon atoms, from 1 to 3 carbon atoms, or 1 to 2 carbon atoms. Examples of alkyl moieties include groups such as methyl, ethyl, n-propyl, isopropyl, n-butyl, tert-butyl, isobutyl, sec-butyl, and the like.

Aspects of the disclosure are described in greater detail by way of specific examples. The following examples are offered for illustrative purposes, and are not intended to limit the disclosure in any manner. Those of skill in the relevant art will readily recognize a variety of parameters can be changed or modified to yield essentially the same results.

EXAMPLES

The invention will now be more particularly described with reference to the following non-limiting Examples and the accompanying drawings.

The X-ray diffraction data reported in the Examples herein were collected with a Bruker D4 Endeavor instrument in continuous mode using Cu Kα radiation with a step size of 0.01796 degrees with the VANTEC-1 gaseous detector with 50 mm×16 mm active area. The interplanar spacings, d-spacings, were calculated in Angstrom units, and the relative intensities of the lines, $I/I_o$ is the ratio of the peak intensity to that of the intensity of the strongest line, above background. The intensities are uncorrected for Lorentz and polarization effects. The location of the diffraction peaks in 2-theta, and the relative peak area intensities of the lines, I/I(o), where Io is the intensity of the strongest line, above background, were determined with the MDI Jade peak search algorithm. It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

Synthesis of Organic Structure Directing Agent (Compound I)

As discussed above, the organic structure directing agents, Q or Compound I that are useful in the synthesis of EMM-28 can be produced from 1,3-bis(halomethyl)benzenes.

A suitable (prophetic) synthesis regimen for a compound of Compound I from 1,3-bis(chloromethyl)benzene is described below.

Preparation of 3,3'-(1,3-phenylene)dipropionic acid

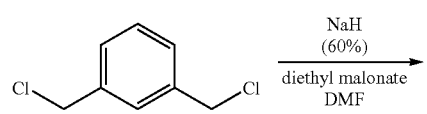

NaH (60%)
diethyl malonate
DMF

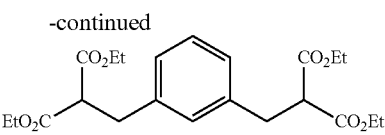

An oven dried 2 L 3-necked jacketed flask equipped with mechanical stirrer is assembled hot, and cooled under flowing $N_2$ then charged with 67.2 g (1680 mmol) 60% sodium hydride in mineral oil. The contents are cooled to 0° C. with circulating glycol-water and 670 mL anhydrous DMF added via cannula. 360 mL (2.37 mole) diethylmalonate is added dropwise to the flask over 40 minutes. About half way through the addition, the chiller is drained and the temperature allowed to rise to 35° C. All the NaH had dissolved and the solution is clear. To this is added 102.1 g (582 mmol) 1,3-bis(chloromethyl)benzene all at once. The temperature rose to 65° C. and solid formed. After heating with steam for 1 hour, the flask is cooled to 0° C. and a solution of 37 mL concentrated HCl in 1000 mL $H_2O$ is added. The contents of the flask are then transferred to a separatory funnel, where the viscous lower layer is withdrawn as product. After removing volatiles on a rotary evaporator, the product is distilled at 125° C. @ 250 mTorr to produce 228 g (86%) white liquid product.

Preparation of tetraethyl 2,2'-(1,3-phenylenebis(methylene))dimalonate

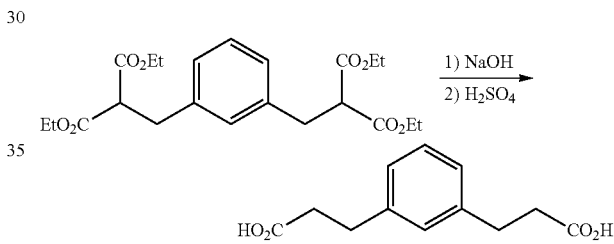

The 3,3'-(1,3-phenylene)dipropionic acid is poured into 121 g (3.02 mol) NaOH in 640 mL $H_2O$ and washed with 25 mL ethanol. The mixture is heated at reflux for 45 min (homogeneous when it reached reflux) then 325 mL is distilled through a 6" Vigreux column. The boiling point of the last 100 mL is 100-101° C. The solution is cooled and 152 g concentrated $H_2SO_4$ dripped in at a rate to just maintain reflux. A bubbler is added and the mixture is heated at reflux until no more $CO_2$ evolved (overnight). There is yellow oil floating in the flask plus some solid. The mixture is poured into 2 L $H_2O$, extracted 2×200 mL diethylether, then the extract is washed 1×200 mL with saturated NaCl and filtered through 4 Å molecular sieve. The solvent is removed on a rotary evaporator and the remaining volatiles distilled at 120° C. at 260 mTorr to give 110.5 g (100%) pale tan wax. The product may be confirmed by $^{13}C$ NMR and $^1H$ NMR spectra. The product had the expected $^{13}C$ NMR and $^1H$ NMR spectra.

Preparation of 3,3'-(1,3-phenylene)bis(propan-1-ol)

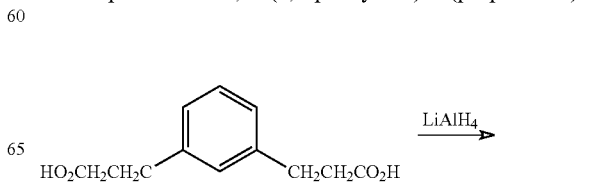

-continued

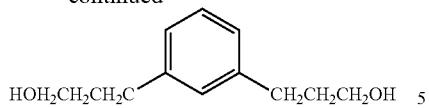

An oven dried 3 L 3-necked jacketed flask equipped with equalizing dropping funnel, reflux condenser, and mechanical stirrer is assembled hot and cooled under flowing $N_2$ then charged with 920 g anhydrous THF and 30.55 g (805 mmol) $LiAlH_4$ pellets. The mixture is stirred for 30 min then 110 g (498 mmol) of tetraethyl 2,2'-(1,3-phenylenebis(methylene))dimalonate in 250 g anhydrous THF is added dropwise over 1 hour. Three quarters of the way through the addition the solid became very hard to stir. Addition of 300 mL anhydrous THF made the slurry stirrable again. The reaction is exothermic throughout the addition and produced gas ($H_2$) throughout the addition. The mixture is refluxed 20 min, cooled to 0° C. and quenched with 150 mL 1:1 v/v $H_2O$:THF then 42.7 g NaOH in 427 g $H_2O$. The product is filtered through a Buchner funnel and the solid residue washed with 500 mL diethylether. After removal of the solvent on a rotary evaporator, remaining volatiles are removed by vacuum distillation at 100° C. @ 2 mTorr to give 70.2 g (74%) white, semisolid. The product may be confirmed by $^{13}C$ NMR and $^1H$ NMR spectra.

Preparation of 1,3-phenylenebis(propane-3,1-diyl) bis(4-methylbenzenesulfonate)

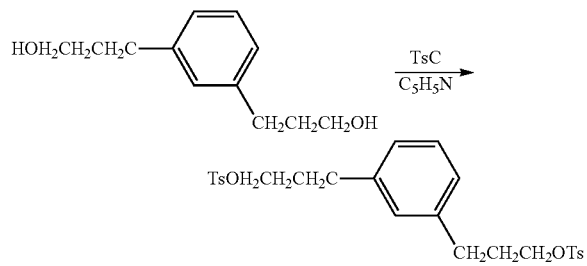

A 1 L jacketed flask containing 70.2 g (362 mmol) of 3,3'-(1,3-phenylene)bis(propan-1-ol), 260 mL pyridine, and 480 mL $CHCl_3$ (amylene stabilized) is cooled to −5° C. with circulating glycol-water and 138 g (723 mmol) p-toluenesulfonyl chloride added all at once. The temperature rose to 25° C., chilling is stopped and, after stirring for 45 min, the mixture is poured into 1000 mL $H_2O$+212 mL conc. HCl. The lower layer is separated and washed with 100 mL saturated NaCl solution. Residual solvent is removed on a rotary evaporator, and the remaining volatiles are removed by vacuum distillation at 60° C.@650 mTorr to give 171 g (94%) brown resin. The product may be confirmed by $^{13}C$ NMR and $^1H$ NMR.

Preparation of 1,3-bis(3-(pyrrolidin-1-yl) propyl)benzene

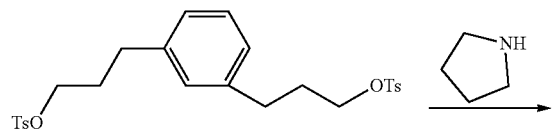

-continued

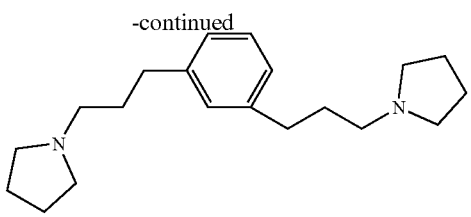

116 g (231 mmol) of 1,3-phenylenebis(propane-3,1-diyl) bis(4-methylbenzenesulfonate) is treated with 160 mL (1.92 mol) pyrrolidine. The mixture darkened and an exotherm took the temperature to boiling. The mixture is poured, hot, into 800 mL $H_2O$ containing 80 g NaOH. The layers separated and the aqueous layer is extracted with 1×350 mL diethylether. The organic layers are combined, washed 1×200 mL $H_2O$, and the volatiles removed on a rotary evaporator before the product is distilled at 220° C.@180 mTorr to give 54.9 g yellow oil plus solid. GCMS shows the expected product with m/z=300 (large M-1 peak) but it is heavily contaminated with 1-tolylpyrrolidine. The product may be confirmed by $^{13}C$ NMR and $^1H$ NMR.

Preparation of 1,1'-(1,3-phenylenebis(propane-3,1-diyl))bis(1-ethylpyrrolidin-1-ium) hydroxide

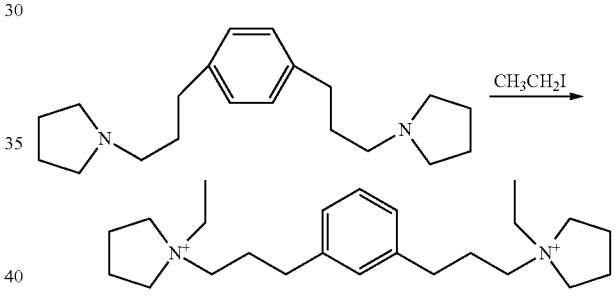

The 1,3-bis(3-(pyrrolidin-1-yl)propyl)benzene is dissolved in 150 mL acetone in an Erlenmeyer flask and 40 mL (680 mmol) iodoethane added gradually over about 15 min. The solution reached gentle reflux and much solid precipitated. The flask is stoppered, wrapped in Al foil, allowed to stand for two days at room temperature, filtered, washed with diethylether, and dried to constant weight at 65° C. to give 77.3 g pink solid (94% based on estimated purity of diamine). This is ion exchanged in batch mode to give 371 g pale yellow solution. Titration of 2.62 mL of this solution diluted to 25 mL took 6.19 mL to titrate 91.1 mg potassium phthalate. This calculates for 12.5% as the dihydroxide. Integration of the $^1H$ NMR organic hydrogen signals against water signal gave 12.7% as the dihydroxide. The product may be confirmed by $^{13}C$ NMR and $^1H$ NMR.

In a modification of the above (prophetic) synthesis regimen for the dication of Compound I, 1,3-phenylenebis (propane-3,1-diyl)bis(4-methylbenzenesulfonate) is reacted with 1-ethylpyrrolidine in chloroform or acetonitrile to produce the dication directly without intermediate production of the diamine.

Additionally and alternatively, another suitable (prophetic) synthesis regimen for a compound of Compound I from 1,3-diiodobenzene is described below.

Preparation of 3,3'-(1,3-phenylene)bis(prop-2-yn-1-ol)

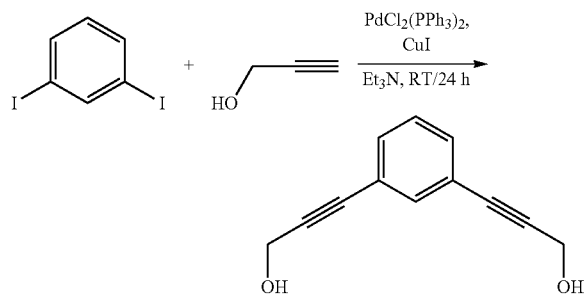

To an oven dried 2 L 3-neck round bottom flask attached to a mechanical stirrer is added 1,3-diiodobenzene (36.0 g; 109.1 mmol) to 225 mL of dry triethylamine under nitrogen. To the light brown solution is added bis(triphenylphosphine) palladium(II) dichloride (4.2 g; 6.0 mmol, 0.05 mol %) followed by copper (I) iodide (0.33 g; 1.74 mmol, 0.015 mol %). The dark green mixture is stirred for 5 minutes. Propargyl alcohol (21.5 mL; 371.2 mmol) is added dropwise via an addition funnel. A slight exotherm is noticed after the addition. The dark brown mixture is stirred for 3 hours at room temperature. TLC (5% ethyl acetate/hexane UV detection) indicated no starting material remained. The reaction is stirred overnight, 1,500 mL of ethyl acetate is added and it is stirred for an additional 24 hours. The reaction mixture is filtered and the filtrate is concentrated in vacuo to recover 30.4 g of a brown oil. The crude product is purified on silica gel using a continuous gradient of 40-100% ethyl acetate/hexane to recover 15.0 g (74%) of desired product. The product may be confirmed by $^{13}C$ NMR and $^1H$ NMR spectra.

Preparation of 3,3'-(1,3-phenylene)bis(propan-1-ol)

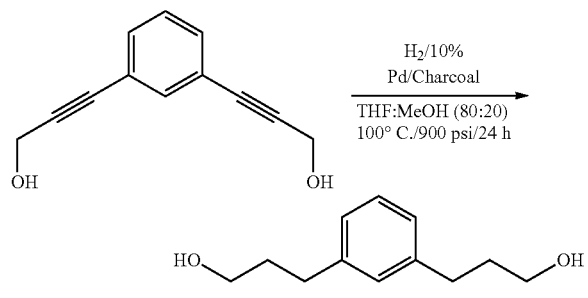

3,3'-(1,3-phenylene)bis(prop-2-yn-1-ol) (2.0 g; 10.7 mmol) is dissolved in 11 mL of anhydrous methanol and placed in a TEFLON® lined autoclave. A slurry of palladium on charcoal (0.4 g; 10% palladium on charcoal) in 40 mL of dry THF is added to the liner over a blanket of nitrogen. The autoclave is closed and pressurized with $H_2$. After 24 hours the reaction solution is filtered through a pad of Celite. The filtrate is concentrated in vacuo to recover 2.1 g (100%) of crude desired product. This product is taken forward without purification. The product may be confirmed by $^{13}C$ NMR and NMR spectra.

Preparation of 1,3-phenylenebis(propane-3,1-diyl) bis(4-methylbenzenesulfonate)

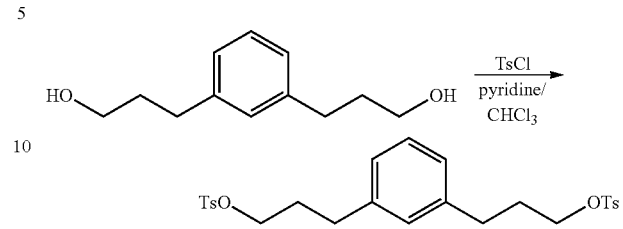

In a dry 25 mL vial with a septum is added 3,3'-(1,3-phenylene)bis(propan-1-ol) (0.2 g; 1.0 mmol) dissolved in 2.0 mL of anhydrous chloroform at room temperature under nitrogen. Pyridine (0.17 mL; 2.1 mmol) is added and the solution is cooled to 0° C. (ice-bath). p-toluenesulfonyl chloride (0.43 g; 2.2 mmol) is added and the light orange solution is allowed to warm to room temperature. After 24 hours the reaction is diluted with 10 mL of 5% HCl and the layers are separated. The organic layer is washed with 10 mL of brine and pre-adsorbed onto silica. The crude product is purified on silica using a continuous gradient of 0 to 100% ethyl acetate/hexane to recover 0.28 g (55%) of the desired compound. The product may be confirmed by $^{13}C$ NMR and $^1H$ NMR.

Preparation of 1,1'-(1,3-phenylenebis(propane-3,1-diyl)bis(1-ethylpyrrolidin-1-ium) 4-methylbenzenesulfonate

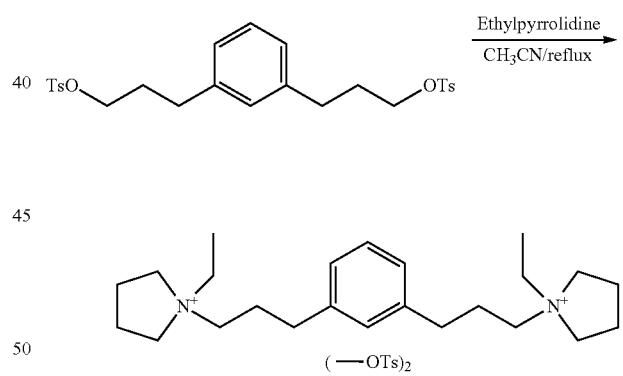

In a dry 20 mL vial with a relief cap and stir bar is added 1.0 g (1.9 mmol) of the 1,3-phenylenebis(propane-3,1-diyl) bis(4-methylbenzenesulfonate) under nitrogen. 2 mL of dry acetonitrile is added and the pale yellow solution is stirred for 5 minutes. Ethylpyrrolidine (0.64 mL; 6.0 mmol) is added dropwise and the solution is stirred at room temperature for one hour. TLC (2:1 hexane:ethyl acetate, UV detection) indicated that starting material remained. The solution is heated to 80° C. After one hour TLC indicated the starting material is consumed. The reaction is cooled to room temperature and stored overnight. The reaction solution is concentrated in vacuo at 45° C. to recover 1.2 g (96%) of the desired product. The product may be confirmed by $^{13}C$ NMR and $^1H$ NMR.

Preparation of 1,1'-(1,3-phenylenebis(propane-3,1-diyl)bis(1-methylpyrrolidin-1-ium) hydroxide

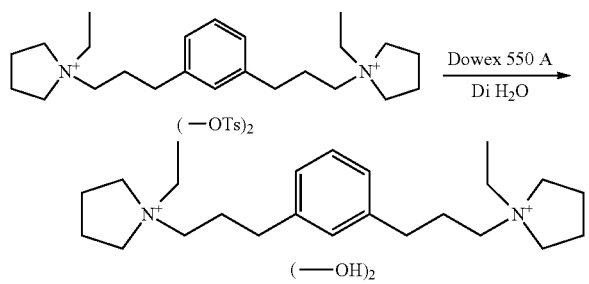

545 g of Dowex Monosphere 550A resin is placed into a 500 mL Nalgene screw cap bottle. The resin is rinsed 3×500 mL with deionized water to remove any fines. 27.3 g (40.5 mmol) of the 1,1'-(1,3-phenylenebis(propane-3,1-diyl))bis(1-methylpyrrolidin-1-ium) 4-methylbenzenesulfonate is dissolved in 100 mL of deionized water and added to the Nalgene container. Deionized water is added to the container until 80% filled. The top of the container is closed and taped. The container is placed on a mechanical roller overnight to facilitate the anion exchange. The slurry is filtered through a Buchner funnel and rinsed with deionized water until pH 9. The aqueous solution is concentrated in vacuo at 40° C. to the desired concentration to afford the dihydroxide. The product may be confirmed by $^{13}C$ NMR and $^1H$ NMR spectra.

Example 1: Synthesis of EMM-41

EMM-41 was first observed from syntheses performed in a 1.5 mL stainless steel reactors tumbled at 150° C. for 10 and 28 days in low water syntheses in the presence of the SDA (in its hydroxide form), hydrogen fluoride and zeolite seeds from ITQ-24, ITQ-33 or no seeds. Tetramethylorthosilicate (TMOS) was the silica source. The SDA(OH)$_2$ was Compound I in its hydroxide form where both of the anions were hydroxide. SDA also supplied the hydroxide source. The composition of the synthesis mixture is shown in Table 11, below. The products were isolated by centrifugation, resuspension in deionized water, and then another centrifugation. This was repeated three times. Examples 1A to 1F produced a powder XRD pattern which could not be matched with any known zeolite. This XRD pattern was designated as pure EMM-41. FIG. 1 shows the XRD pattern of the pure phase EMM-41.

TABLE 11

| | Component/Reaction Conditions | | | | | |
|---|---|---|---|---|---|---|
| Example | OH$^-$/Si (molar) | H$_2$O/Si (molar) | F$^-$/Si (molar) | SDA(OH)$_2$/Si (molar) | Seed | Crystallization Temp/Time |
| 1A | 0.5 | 4 | 0.5 | 0.25 | none | 150° C./672 h |
| 1B | 0.5 | 4 | 0.5 | 0.25 | ITQ-24 | 150° C./672 h |
| 1C | 0.5 | 4 | 0.5 | 0.25 | ITQ-33 | 150° C./672 h |
| 1D | 0.5 | 4 | 0.5 | 0.25 | none | 150° C./240 h |
| 1E | 0.5 | 4 | 0.5 | 0.25 | ITQ-24 | 150° C./240 h |
| 1F | 0.5 | 4 | 0.5 | 0.25 | ITQ-33 | 150° C./240 h |

Example 2: Synthesis of EMM-41 with Varying H$_2$O/SiO$_2$ Molar Ratios in Reaction Mixture 4.38 grams of a 23.81 wt % solution of the SDA (in its hydroxide form) were added to 1.62 g tetramethylorthosilicate (TMOS) and vigorously stirred overnight in 10-ML Teflon liners. The 10 mL TEFLON® reactors were placed in a freeze drier and all water removed. The dried product was then re-slurried with varying amounts of distilled water and 20 wt % Hydrofluoric acid solution. The reactors were placed in a tumbling oven at 150° C. for 12 days. The products were then centrifuged/washed (3×) and dried. The composition of the synthesis mixture and the results of this Example 2 are shown in Table 12, below. As can be seen in Table 12, the synthesis with H$_2$O/SiO$_2$ of 5 and 7 both yielded EMM-41, whereas the syntheses with H$_2$O/SiO$_2$ molar ratios of 10, 14 and 18 failed to make the EMM-41 phase and were amorphous. The powder XRD pattern of Examples 2A1, 2A2 and 2B1 were consistent with EMM-41 (not shown) were consistent with EMM-41.

TABLE 12

| Component/Product | Example | | | | | |
|---|---|---|---|---|---|---|
| Morphology | 2A1 | 2A2 | 2B1 | 2B2 | 2C1 | 2C2 |
| SDA | 4.38 g | 4.38 g | 4.38 g | 4.38 g | 4.38 g | 4.38 g |
| TMOS | 1.62 g | 1.62 g | 1.62 g | 1.62 g | 1.62 g | 1.62 g |

TABLE 12-continued

| Component/Product | Example | | | | | |
|---|---|---|---|---|---|---|
| Morphology | 2A1 | 2A2 | 2B1 | 2B2 | 2C1 | 2C2 |
| EMM-41 Seeds | 6.38 mg | 6.38 mg | 6.38 mg | 6.38 mg | 6.38 mg | 6.38 mg |
| $H_2O/SiO_2$ | 5 | 5 (Repeat) | 7 | 10 | 14 | 18 |
| $H_2O$ | 0.53 | 0.53 | 0.91 | 4.50 | 2.25 | 3 |
| HF 20% | 0.53 | 0.53 | 0.53 | 0.53 | 0.53 | 0.53 |
| Product Morphology | EMM-41 | EMM-41 | EMM-41 | Amorphous | Amorphous | Amorphous |

Example 3: Synthesis of EMM-41 with Varying Silica Sources and Si/Al Molar Ratios Experiments were performed (10 ml scale) in the presence of seeds of EMM-41 where the silica source (TMOS, LUDOX® LS-30 or CABOSPERSE®) and the Si/Al molar ratios were simultaneously varied in the reaction mixture. The composition of the synthesis mixture and the Si/Al molar ratios are shown in Table 13, below. The Examples using tetramethylorthosiliocate (TMOS) produced EMM-41, while the other silica sources did not. The powder XRD patterns of Examples 3A1 and 3A2 (not shown) were consistent with EMM-41.

TABLE 13

| | | Reaction Mixture Component | | | | | |
|---|---|---|---|---|---|---|---|
| Example | Silica Source | Amount of SDA-(OH)$_2$ | Al-Nitrate 15 wt % (g) | Si Sources (g) | Actual Back Water Added (g) | 20 wt % HF (g) | EMM-41 Seeds (g) | Si/Al Ratio (Molar) |
| 3A1 | TMOS | 4.040 | 0.460 | 1.490 | 1.24 | 0.50 | 0.006 | 30 |
| 3A2 | TMOS | 4.170 | 0.290 | 1.540 | 1.37 | 0.50 | 0.006 | 50 |
| 3B1 | LUDOX ® LS-30 | 3.760 | 0.430 | 1.800 | 0.78 | 0.46 | 0.006 | 30 |
| 3B2 | LUDOX ® LS-30 | 3.870 | 0.270 | 1.850 | 0.91 | 0.47 | 0.006 | 50 |
| 3C1 | CABOSPERSE ™ | 3.040 | 0.350 | 2.610 | 0.05 | 0.37 | 0.004 | 30 |
| 3C2 | CABOSPERSE ™ | 3.110 | 0.210 | 2.670 | 1.05 | 0.38 | 0.004 | 50 |

Example 4: EMM-41 Synthesis with Varying Silica Sources Only

For this Example 4, the above Example 3 was repeated, except that only a silica source (TMOS, LUDOX® LS-30 or CABOSPERSE®) was utilized in the reaction mixture (i.e., no source of aluminum). The composition of the synthesis mixture and the Si/Al molar ratios are shown in Table 14, below. In this Example 4, the reaction mixture comprising the SDA and silica source for each experiment were allowed to sit and digest for 3 days at room temperature prior to being placed in freeze drier to remove the water. The powder XRD patterns of all of the experiments in Example 4 (not shown) were consistent with EMM-41.

Example 5: Characterization of EMM-41 as-Made and Calcined

Figure 2:
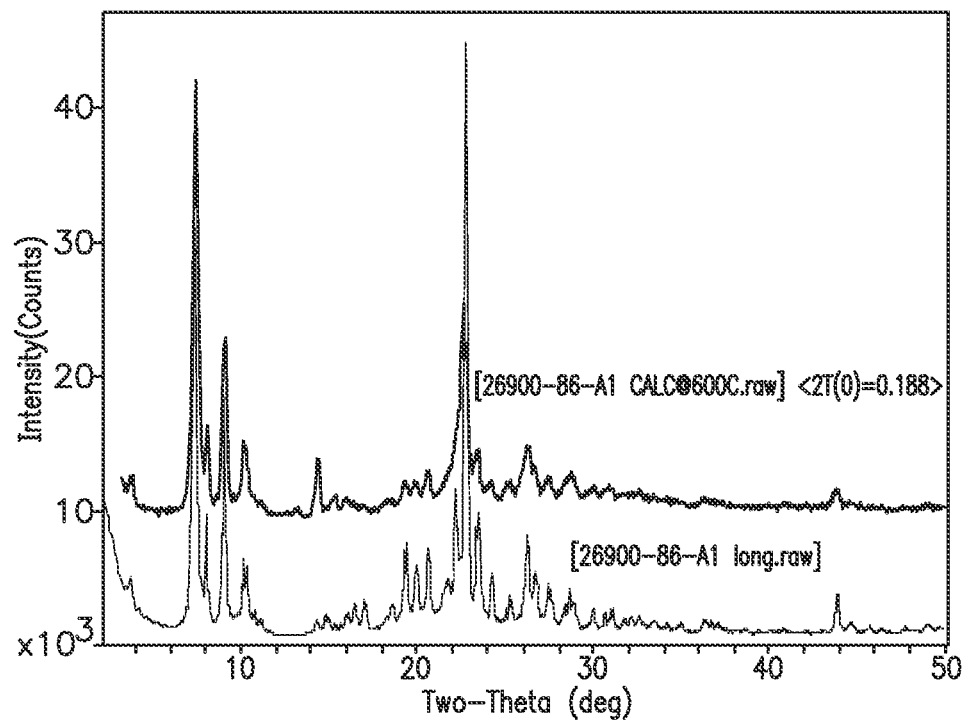
FIG. 2 shows a powder XRD pattern for as-made EMM-41 (bottom) and calcined EMM-41 (top) materials of Example 5.

For this Example 5, the above Example 2A2 was repeated, except that the zeolite seeds used were ITQ-24. The as-made material was calcined to 600° C. to remove the organic SDA (Q) using standard calcination protocol. Tables 15A and 15B show a listing of the peak positions and their intensities of the XRD for the as-made and calcined products, respectfully. The powder XRD patterns for the as-made product and the calcined product are shown graphically in FIG. 2, confirming that the material synthesized was EMM-41.

TABLE 15A

| As-made EMM-41 | | |
|---|---|---|
| at 2-Theta degrees | d-spacing (Å) | Area % |
| 3.69 | 23.96 | 5 |
| 7.25 | 12.19 | 22 |
| 7.42 | 11.90 | 87 |
| 8.04 | 10.98 | 13 |
| 9.06 | 9.76 | 40 |
| 10.11 | 8.74 | 8 |
| 10.32 | 8.57 | 13 |
| 10.78 | 8.20 | 3 |
| 11.15 | 7.93 | 2 |

TABLE 14

| Example | Si Source | Amount of SDA | Si Sources (g) | Actual Back Water to Add (g) | Add HF 20 wt % (g) | seeds (mg) |
|---|---|---|---|---|---|---|
| 5A1 | ULTRASIL ® | 5.160 | 0.830 | 0.45 | 0.63 | 7.5 |
| 5A2 | ULTRASIL ® | 5.160 | 0.830 | 0.06 | 0.63 | 7.5 |
| 5B1 | LUDOX ® LS-30 | 4.050 | 1.940 | 1.14 | 0.50 | 5.9 |
| 5B2 | LUDOX ® LS-30 | 4.050 | 1.940 | 0.09 | 0.50 | 5.9 |
| 5C1 | CABOSPERSE ™ | 3.230 | 2.770 | −0.81 | 0.40 | 4.7 |
| 5C2 | CABOSPERSE ™ | 3.230 | 2.770 | −0.21 | 0.40 | 4.7 |

TABLE 15A-continued

As-made EMM-41

| at 2-Theta degrees | d-spacing (Å) | Area % |
|---|---|---|
| 14.32 | 6.18 | 1 |
| 14.44 | 6.13 | 1 |
| 14.87 | 5.95 | 3 |
| 15.06 | 5.88 | 1 |
| 16.02 | 5.53 | 2 |
| 16.14 | 5.49 | 1 |
| 16.51 | 5.36 | 7 |
| 17.03 | 5.20 | 3 |
| 17.10 | 5.18 | 3 |
| 18.25 | 4.86 | 2 |
| 18.62 | 4.76 | 4 |
| 19.39 | 4.57 | 17 |
| 19.99 | 4.44 | 11 |
| 20.67 | 4.29 | 11 |
| 21.54 | 4.12 | 2 |
| 21.77 | 4.08 | 6 |
| 22.27 | 3.99 | 25 |
| 22.79 | 3.90 | 100 |
| 23.50 | 3.78 | 20 |
| 24.30 | 3.66 | 6 |
| 25.24 | 3.53 | 4 |
| 26.23 | 3.39 | 27 |
| 26.67 | 3.34 | 11 |
| 27.41 | 3.25 | 10 |
| 27.63 | 3.23 | 2 |
| 28.31 | 3.15 | 3 |
| 28.62 | 3.12 | 5 |
| 28.87 | 3.09 | 6 |
| 29.97 | 2.98 | 4 |
| 30.64 | 2.92 | 2 |
| 31.02 | 2.88 | 3 |
| 31.73 | 2.82 | 2 |
| 32.13 | 2.78 | 3 |
| 32.58 | 2.75 | 2 |
| 32.81 | 2.73 | 1 |
| 33.42 | 2.68 | 2 |
| 34.21 | 2.62 | 1 |
| 34.93 | 2.57 | 1 |
| 36.35 | 2.47 | 3 |
| 36.73 | 2.45 | 1 |
| 37.08 | 2.42 | 2 |

TABLE 15

B-Calcined EMM-41

| at 2-Theta | d-spacing (Å) | Area (%) |
|---|---|---|
| 3.68 | 24.02 | 8 |
| 7.35 | 12.03 | 100 |
| 7.38 | 11.97 | 81 |
| 8.02 | 11.01 | 18 |
| 9.04 | 9.78 | 47 |
| 10.10 | 8.75 | 9 |
| 10.28 | 8.60 | 22 |
| 10.75 | 8.22 | 1 |
| 11.09 | 7.97 | 1 |
| 13.22 | 6.69 | 1 |
| 14.39 | 6.15 | 12 |
| 15.35 | 5.77 | 4 |
| 16.05 | 5.52 | 5 |
| 16.48 | 5.38 | 2 |
| 17.05 | 5.20 | 1 |
| 18.21 | 4.87 | 1 |
| 18.59 | 4.77 | 2 |
| 19.37 | 4.58 | 5 |
| 19.94 | 4.45 | 5 |
| 20.65 | 4.30 | 7 |
| 21.73 | 4.09 | 6 |
| 22.25 | 3.99 | 12 |
| 22.77 | 3.90 | 47 |
| 23.48 | 3.79 | 10 |
| 24.29 | 3.66 | 3 |

TABLE 15-continued

B-Calcined EMM-41

| at 2-Theta | d-spacing (Å) | Area (%) |
|---|---|---|
| 25.22 | 3.53 | 3 |
| 26.20 | 3.40 | 14 |
| 26.64 | 3.34 | 6 |
| 27.42 | 3.25 | 5 |
| 28.42 | 3.14 | 3 |
| 28.64 | 3.11 | 0 |
| 28.87 | 3.09 | 5 |
| 29.95 | 2.98 | 4 |
| 30.64 | 2.92 | 2 |
| 30.99 | 2.88 | 2 |
| 32.63 | 2.74 | 3 |
| 33.45 | 2.68 | 1 |
| 34.41 | 2.60 | 2 |
| 36.50 | 2.46 | 6 |

Various modifications of the disclosure, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

The invention claimed is:

1. A EMM-41 crystalline material having at least five (5) XRD peaks selected from Table 1A:

TABLE 1A

| degrees 2-theta (±0.2) | d-spacing (Å) | relative integrated intensity [100 × I/(Io)] |
|---|---|---|
| 7.35 | 12.03 | composite |
| 7.38 | 11.97 | Composite (100) |
| 9.04 | 9.78 | 20-40 |
| 10.28 | 8.60 | 9-20 |
| 14.39 | 6.15 | 3-10 |
| 22.77 | 3.90 | 20-40 | wherein the XRD peaks are defined as peaks collected with a Bruker D4 Endeavor instrument in continuous mode using Cu Kα radiation with a step size of 0.01796 degrees with a gaseous detector having a 50 mm×16 mm active area.

2. The crystalline material of claim 1 having at least six (6) XRD peaks selected from Table 1B:

TABLE 1B

| degrees 2-theta (±0.2) | d-spacing (Å) | relative integrated intensity [100 × I/(Io)] |
|---|---|---|
| 7.35 | 12.03 | composite |
| 7.38 | 11.97 | composite (100) |
| 8.02 | 11.01 | 5-10 |
| 9.04 | 9.78 | 20-40 |
| 10.28 | 8.60 | 9-20 |
| 14.39 | 6.15 | 3-10 |
| 22.25 | 3.99 | 4-10 |
| 22.77 | 3.90 | 20-40 |
| 26.20 | 3.40 | 5-11 | wherein part or all of a structure directing agent that is present in the material when made is removed.

3. The crystalline material of claim 1 having a micropore volume in the range of about 0.25 to 0.30 cc/g.

4. The crystalline material of claim 1 having a total BET surface area in the range of 400 to 650 m²/g.

5. The crystalline material of claim 1, wherein the material is suitable for adsorbing from 60 to 150 mg/g of n-hexane and/or from 40 to 130 mg/g of 2,3-dimethylbutane and/or from 40 to 130 mg/g of 2,2-dimethylbutane and/or 60 to 90 mg/g of mesitylene, based on the weight of the crystalline material.

6. The crystalline material of claim 1, having a molecular formula of Formula A:

$$(v)X_2O_3:YO_2 \qquad \text{Formula A,}$$

wherein $0.0000 \leq v \leq 0.05$, X is a trivalent element, Y is a tetravalent element and O is oxygen.

7. The crystalline material of claim 1, wherein the molar ratio of Y to X is 1000 when v is 0.0005.

8. The crystalline material of claim 1, wherein the molar ratio of Y to X is 30 to infinity when X is Al.

9. A process for selectively separating one or more desired components of a feedstock from remaining components of the feedstock, the process comprising the steps of:
  (i) contacting said feedstock with a sorbent, at effective sorption conditions, said sorbent comprising an active form of the synthetic porous crystalline material of claim 1, thereby forming a sorbed product and an effluent product; and
  (ii) recovering the one or more desired components from either the sorbed product or the effluent product.

* * * * *